United States Patent
Roussel et al.

(10) Patent No.: US 11,547,523 B2
(45) Date of Patent: Jan. 10, 2023

(54) UNIVERSAL INSTRUMENT HOLDER AND GUIDE FOR ROBOTIC SURGERY

(71) Applicant: MedTech S.A., Montpellier (FR)

(72) Inventors: Eric Roussel, Montferrier sur Lez (FR); Andrei Basturescu, Buchare (RO)

(73) Assignee: MedTech S.A., Montpellier (FR)

(*) Notice: Subject to any disclaimer, the term of this patent is extended or adjusted under 35 U.S.C. 154(b) by 377 days.

(21) Appl. No.: 16/923,712

(22) Filed: Jul. 8, 2020

(65) Prior Publication Data

US 2021/0007827 A1     Jan. 14, 2021

Related U.S. Application Data

(60) Provisional application No. 62/872,485, filed on Jul. 10, 2019.

(51) Int. Cl.
| | |
|---|---|
| *A61B 17/10* | (2006.01) |
| *A61B 90/50* | (2016.01) |
| *A61B 34/20* | (2016.01) |
| *A61B 34/37* | (2016.01) |

(52) U.S. Cl.
CPC .............. *A61B 90/50* (2016.02); *A61B 34/20* (2016.02); *A61B 34/37* (2016.02); *A61B 2034/2055* (2016.02); *A61B 2560/04* (2013.01)

(58) Field of Classification Search
CPC ........ A61B 2034/2055; A61B 2560/04; A61B 34/20; A61B 34/30; A61B 34/37; A61B 90/50; A61B 90/57
See application file for complete search history.

(56) References Cited

U.S. PATENT DOCUMENTS

| | | |
|---|---|---|
| 4,765,669 A | 8/1988 | Meier |
| 8,884,618 B2 | 11/2014 | Mahfouz |
| 9,675,461 B2 | 6/2017 | Mahfouz |
| (Continued) | | |

FOREIGN PATENT DOCUMENTS

| | | |
|---|---|---|
| CN | 109646091 | 4/2019 |
| FR | 2882514 | 9/2006 |
| WO | 2021005177 | 1/2021 |

OTHER PUBLICATIONS

"International Application Serial No. PCT EP2020 069433, International Search Report dated Dec. 8, 2020", 6 pages.
(Continued)

*Primary Examiner* — Insa Sadio
(74) *Attorney, Agent, or Firm* — Schwegman Lundberg & Woessner, P.A.

(57) ABSTRACT

An instrument holder assembly for use with a robotic surgical system can comprise one or more modules for holding or guiding an instrument. Each module can comprise a variable diameter jaw having movable teeth configured to hold or guide different sized instruments. Each module can be attached to opposite ends of a main shaft that can couple to an arm of the robotic surgical system. A central passage can extend through each module and the main shaft and the variable diameter jaws can constrict the central passage. Teeth of the variable diameter jaws can be biased to a closed or opened position. A tensioner tool can be used to hold biasing elements in position so that the teeth can be loaded into the module. The teeth can be loaded into slots of the module using a tooth holder device.

20 Claims, 24 Drawing Sheets

(56) References Cited

U.S. PATENT DOCUMENTS 9,782,224 B2 * 10/2017 Piccin ..................... B25J 15/12
2008/0086150 A1 4/2008 Mathis et al.
2017/0312035 A1 11/2017 May et al.
2018/0271511 A1 * 9/2018 Stanton .............. A61B 17/3439

OTHER PUBLICATIONS

"International Application Serial No. PCT EP2020 069433, Written Opinion dated Dec. 8, 2020", 9 pages.
"International Application Serial No. PCT EP2020 069433, International Preliminary Report on Patentability dated Jan. 20, 2022", 11 pages.

* cited by examiner

UNIVERSAL INSTRUMENT HOLDER AND GUIDE FOR ROBOTIC SURGERY

CLAIM OF PRIORITY

This application claims the benefit of U.S. Provisional Patent Application Ser. No. 62/872,485, filed on Jul. 10, 2019, the benefit of priority of which is claimed hereby, and which is incorporated by reference herein in its entirety.

TECHNICAL FIELD

This document pertains generally, but not by way of limitation, to devices and methods for robot-assisted surgical procedures, such those involving the use of articulating arms that can be moved about multiple axes. More specifically, but not by way of limitation, the present application relates to holders and guides that can be used to position instruments with robotic surgical systems.

BACKGROUND

Imaging of anatomical features can be useful in preparing for and performing surgical procedures. In some surgical procedures it can be desirable to register the shape of the anatomy in the obtained images with another frame of reference, such as the physical space of an operating room. The physical space of the operating room can be correlated to a frame of reference for a robotic surgical system. Robotic surgical arms are used to hold various instruments in place in a desired orientation relative to both the anatomy and operating room during a procedure so that movement of an instrument in the operating room relative to the anatomy can be tracked on the anatomic imaging based on movement of the robotic surgical arm. It is, therefore, desirable to precisely mount instruments to the robotic surgical arm. An example of an adjustable instrument holder is described in Pub. No. US 2008/0086150 to Mathis et al.

Overview

The present inventors have recognized, among other things, that a problem to be solved with traditional robotic instrument holders can include the requirement of having to change fixed-diameter instrument holders during robotic surgical procedures. During surgeries involving a robotic surgical system, it can be desirable to precisely guide a medical instrument along a planned trajectory based on medical images. In order to maintain the trajectory of the instrument, surgeons use guide tubes or other devices that are mounted to a robotic surgical arm. Depending on the medical instrument the surgeon uses during the surgery, different constant diameter guide tubes are used. If the surgeon desires or needs to use a different instrument with a different diameter, it is typically necessary to change the guide tube mounted to the robotic surgical arm each time an instrument change occurs. Such change-over procedures are time-consuming and require a set of guide tubes corresponding to instruments set to be used during the surgery be available and at hand. Additionally, clean-up and sterilization time and costs are increased due to having to clean multiple guide tubes.

The present subject matter can provide a solution to these and other problems, such as by providing adjustable, e.g., adjustable diameter, instrument positioning devices, such as instrument holders and guides. The present subject matter relates to medical instrument holder devices, such as for robotic surgical systems, that have variable passage sizes, e.g., diameters, and methods of assembly-disassembly for such instrument holder devices. The medical instrument holder devices of the present subject matter facilitate installation of various medical instruments with different diameters during a surgical procedure without performing change-over procedures from a robotic surgical arm for different instrument holders. The internal mechanisms of these medical instrument holders allow for precise alignment of the instrument, ease of assembly-disassembly for sterilization purposes and improved ergonomics for the operator. The present subject matter permits the operator to use, during surgeries, only one instrument holder instead of a set of guide tubes with different diameters in order to guide different instruments with different diameters, which saves time and costs during surgeries as well as allowing use of legacy instrument sets within robotic procedures.

In an example, an instrument holder system can comprise a base, a plurality of teeth and a cap. The base can comprise a disk including a central bore, a post extending from the disk along an axis to form an annulus surrounding the central bore, and a plurality of guide slots, each of the plurality of guide slots comprising a disk portion extending in a radial direction along the disk and a post portion extending an axial direction along the post. The plurality of teeth can be positioned in the plurality of guide slots, respectively, and each tooth can comprise a rail for movement in the disk portion, a spoke extending from the rail for movement in the post portion and a tab extending from the rail. The cap can comprise a cover portion configured to cover the base, the cover can include an aperture to receive the post and a plurality of positioning slots disposed in the cover configured to receive the tabs of the plurality of teeth, respectively. Each positioning slot can be disposed oblique to the radial direction such that rotation of the cap causes the rails to move in the disk portions of the plurality of guide slots so that the spokes move relative to the annulus.

In another example, an instrument holder assembly for use with a robotic surgical system can comprise a main shaft for assembling to an arm of the robotic surgical system, a first instrument module and a second instrument module. The main shaft can comprise a first end, a second end and a central passage extending between the first end and the second end. The first instrument module can be couplable to the first end of the main shaft and can comprise a first variable diameter jaw configured to hold or guide a portion of an instrument extending from the central passage at the first end. The second instrument module can be couplable to the second end of the main shaft and can comprise a second variable diameter jaw configured to hold or guide a portion of the instrument extending from the central passage at the second end.

In an additional example, a method of assembling an adjustable, pre-tensioned instrument holder can comprise inserting posts of a tensioner tool into channels of a disk of an instrument holder, positioning the posts against biasing members of the instrument holder, rotating the tensioner tool relative to the instrument holder to move the biasing members with the posts, inserting teeth into slots of the instrument holder, and releasing tension in the biasing members such that the biasing members push the teeth into or away from a passage of the instrument holder.

This overview is intended to provide an overview of subject matter of the present patent application. It is not intended to provide an exclusive or exhaustive explanation of the invention. The detailed description is included to provide further information about the present patent application.

Figure 1:
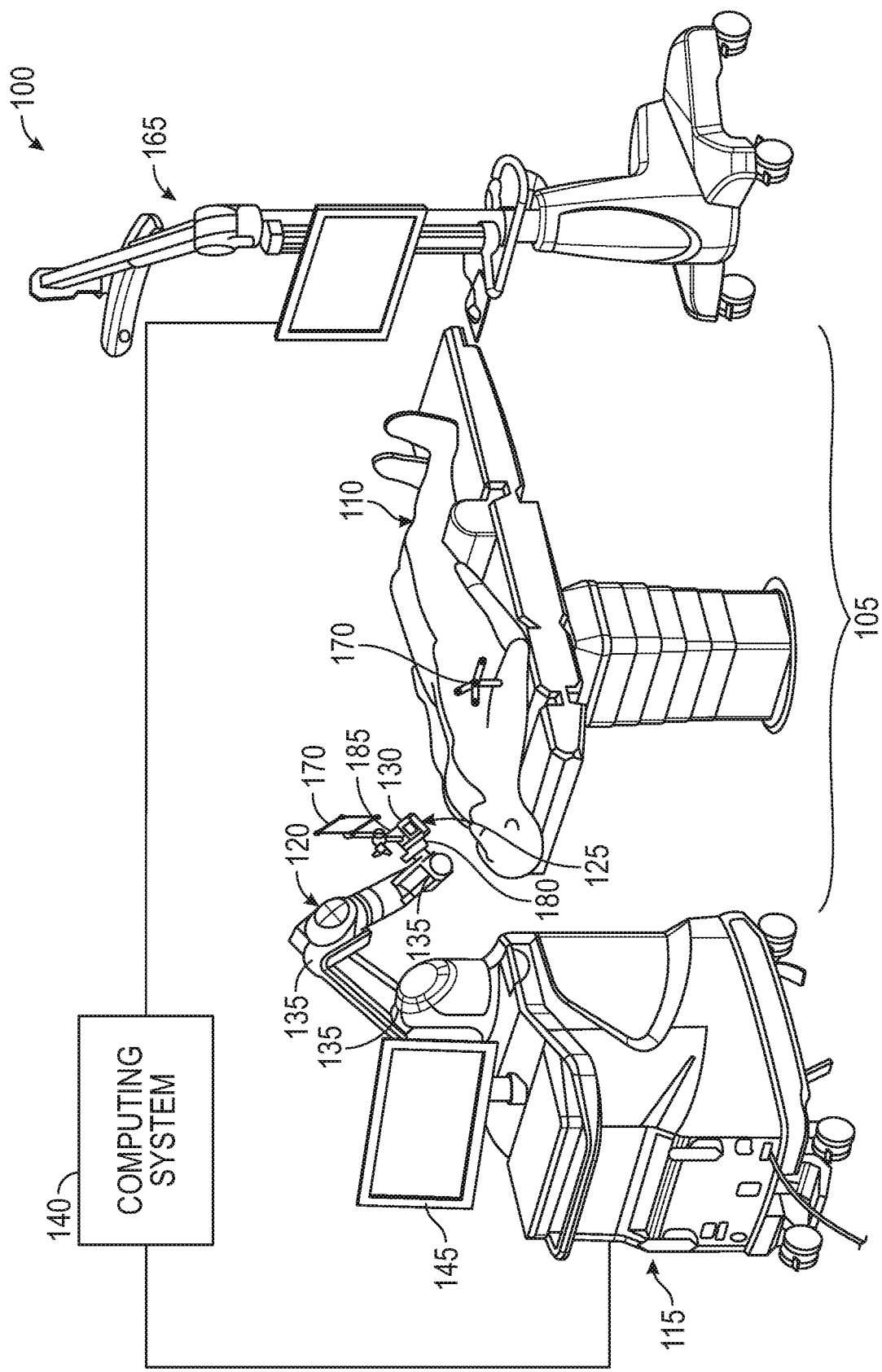
FIG. 1 is a diagrammatic view of an operating room including a robot-assisted surgical system comprising a robotic arm, a computing system and a tracking system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a probe or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with an instrument positioning device, e.g., instrument holder 200 (FIG. 2), to position an instrument in a known orientation relative to surgical area 105 based on a virtual coordinate system determined by computing system 140.

Robotic system 115 can also include computing system 140 that can operate robotic arm 120 and surgical instrument 125. Computing system 140 can include at least memory, a processing unit, and user input devices, as will be described herein. Computing system 140 can also include human interface device 145 for providing images for a surgeon to be used during surgery. Computing system 140 is illustrated as a separate standalone system, but in some examples computing system 140 can be integrated into robotic system 115. Human interface device 145 can provide images, including but not limited to three-dimensional images of bones, glenoid, joints, and the like. Human interface device 145 can include associated input mechanisms, such as a touch screen, foot pedals, or other input devices compatible with a surgical environment.

Computing system 140 can receive pre-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. The virtual model, along with virtual representations of implants, can be used for calculations related to the desired height, depth, inclination angle, or version angle of an implant, stem, surgical instrument, or the like related to be utilized in surgical area 105. In another procedure type, the virtual model can be utilized to determine insertion location, trajectory and depth for inserting an instrument. The virtual model can also be used to determine bone dimensions, implant dimensions, bone fragment dimensions, bone fragment arrangements, and the like. Any model generated, including three-dimensional models, can be displayed on human interface device 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 functions to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to an adjustable instrument holder of the present disclosure. Robotic arm 120 can move the adjustable instrument holder into different positions relative to anatomy of the patient such that an axis of the adjustable instrument holder extends along a desired orientation relative to the anatomy. The adjustable instrument holders of the present application can enable the use of different sized surgical instruments to be held by the robotic arm without requiring change-out of a fixed-sized instrument holder form robotic arm 120.

Figure 2:
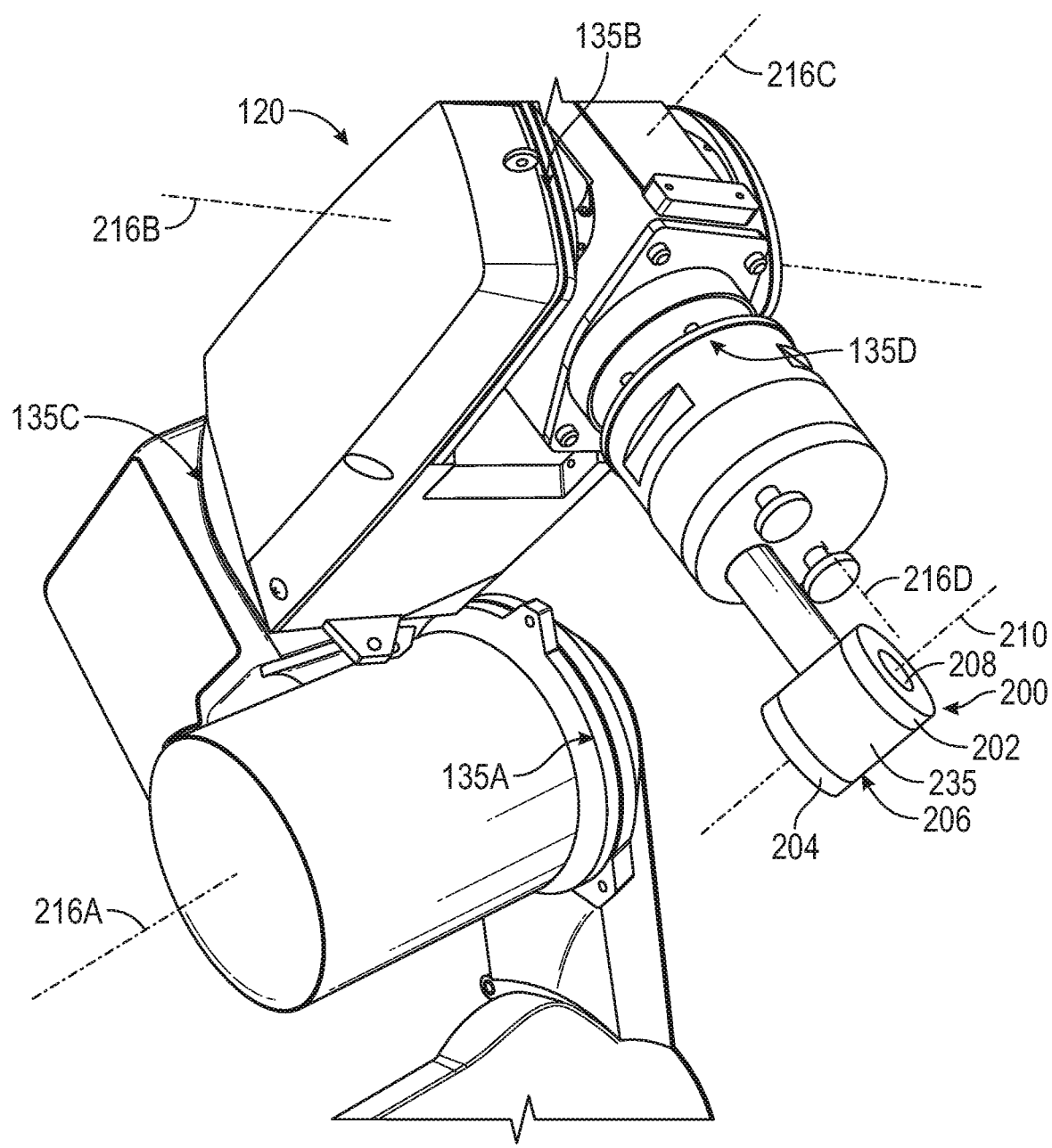
FIG. 2 is a schematic view of the robotic arm of FIG. 1 including an adjustable instrument holder configured to support or guide an instrument along an axis.

FIG. 2 is a schematic view of robotic arm 120 of FIG. 1 including instrument holder 200, which can be positioned by robotic arm 120 relative to surgical area 105 (FIG. 1) in a known orientation. Instrument holder 200 can comprise upper module 202, lower module 204 and shaft 206. Passage 208 can extend through upper module 202, shaft 206 and lower module 204 along axis 210. Instrument holder 200 can be coupled to robotic arm 120 via extension 212 and mounting plate 214.

Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to position instrument holder 200 relative to anatomy of patient 110 (FIG. 1), surgical system 100 (FIG. 1) can manipulate robotic arm 120 automatically by computing system 140 or a surgeon manually operating computing system 140 to move instrument holder 200 to the desired location, e.g., a location called for by a surgical plan to align an instrument relative to the anatomy. For example, robotic arm 120 can be manipulated along axes 216A-216D to position passage 208 of instrument holder 200 along a trajectory for which an instrument is to be guided.

Robotic arm 120 can be separately registered to the coordinate system of surgical system 100, such via use of a tracking element 170. Fiducial markers can additionally be separately registered to the coordinate system of surgical system 100 via engagement with a probe having a tracking element 170 attached thereto. As such, some or all of the components of surgical system 100 can be individually registered to the coordinate system and, if desired, movement of such components can be continuously or intermittently tracked with a tracking element 170.

It can be a difficult task to ensure instruments attached to robotic arm 120 are accurately aligned with patient 110, particularly if multiple instruments have to be successively mounted to robotic arm 120. For example, if instruments are not precisely aligned through the center of an instrument holder, the instrument will not be positioned relative to robotic arm 120 in a location where surgical system 100 understands it to be within the virtual coordinate system. For example, if an instrument is positioned within an instrument holder having a larger passage than the instrument, the instrument can be skewed relative to axis 210 or can be offset in a parallel position from axis 210.

In order to improve the alignment of instruments with axis 210 and to reduce times in changing instruments coupled to robotic arm 120 along axis 210 or other axes, the present application describes various instrument positioning devices, such as instrument holders and guides, that can accommodate different instruments without requiring change-out of the instrument positioning device from robotic arm 120 or recalibration of the instrument holder 200.

In some robotic procedures instruments can be separately tracked using an optical navigation system that, under ideal condition, alleviate the need for precisely maintaining axis 210 through different instrument changes, as the optical navigation system can provide the surgical computer system information to compensate for any changes. However, as optical navigation systems require line of sight with the instruments to be maintained, there is a significant advantage in not requiring instruments to be navigated (or at least not constantly navigated). Accordingly, the ability to precisely maintain axis 210 provides the additional advantage of at least reducing, and possibly eliminating, the need to navigate instruments during a robotic procedure.

Figure 3:
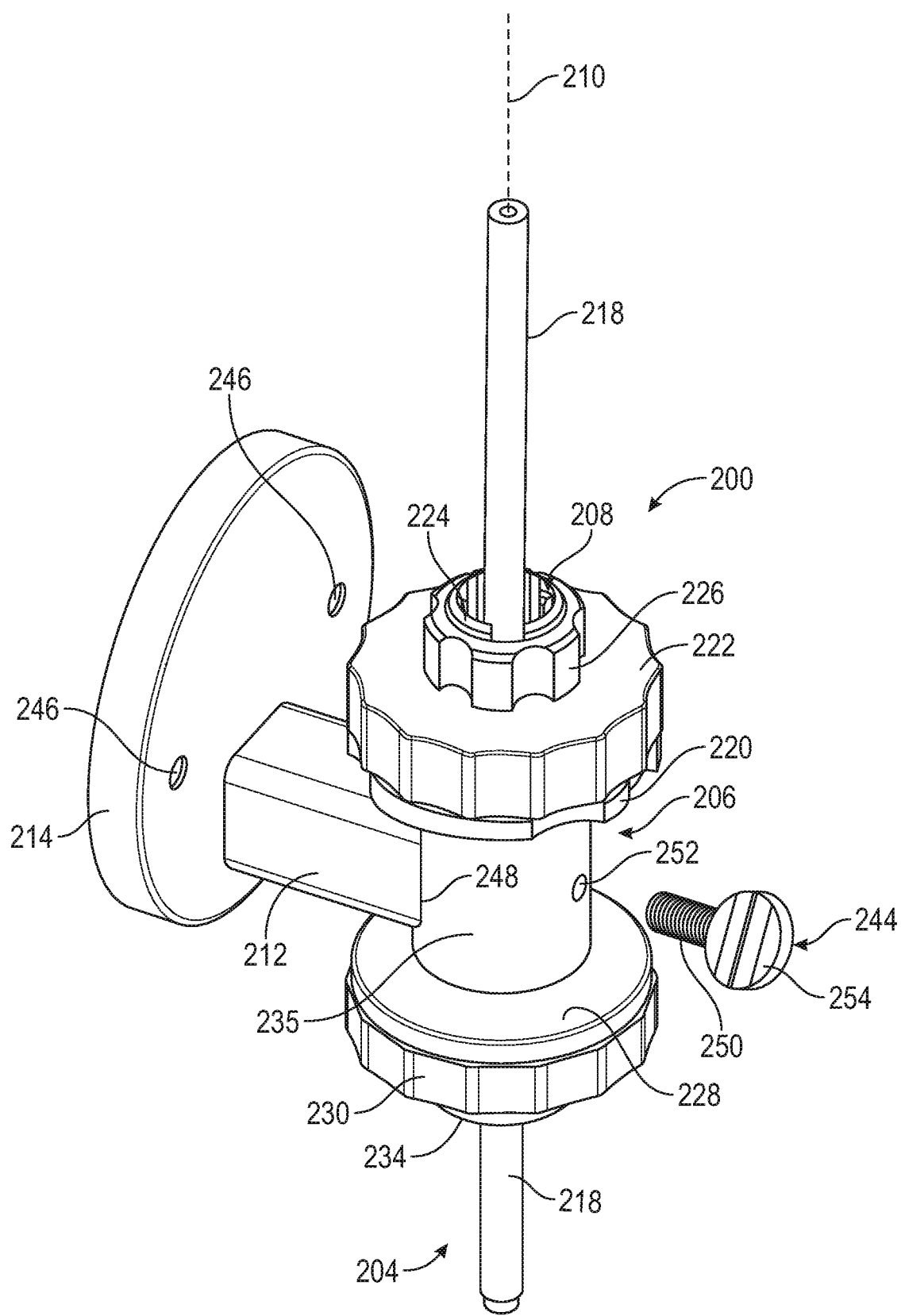
FIG. 3 is a perspective view of an adjustable instrument holder for aligning and holding in-place various medical instruments during surgeries performed with a surgical robot, such as the robot-assisted surgical system of FIGS. 1 and 2.
Figure 4:
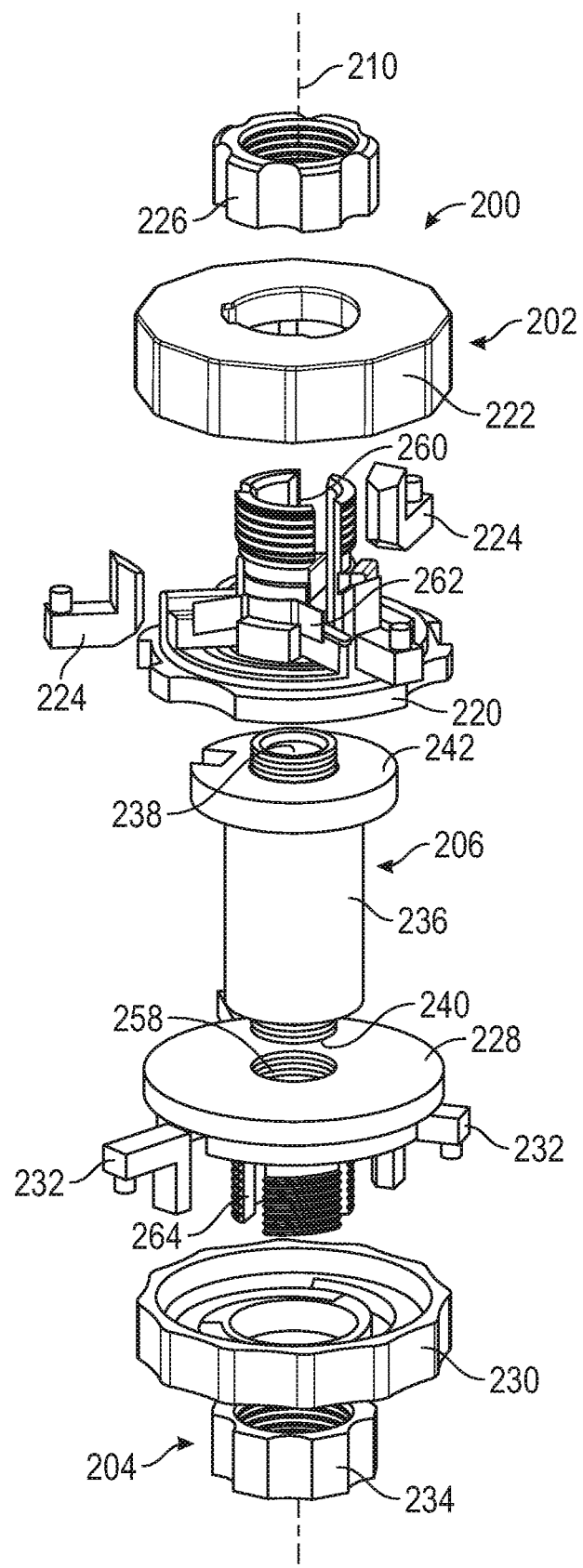
FIG. 4 is a perspective exploded view of the universal diameter adapter holder uncoupled from a robotic arm comprising a first (top) module, a main (middle) shaft and a second (bottom) module.

FIG. 3 is a perspective view of instrument holder 200 comprising first module 202, second module 204, shaft 206 and passage 208. Instrument 218 can be positioned within passage 208. FIG. 4 is a perspective exploded view of instrument holder 200 uncoupled from a robotic arm comprising first (top) module 202, main (middle) shaft 206 and second (bottom) module 204. FIGS. 3 and 4 are discussed concurrently.

First module 202 can comprise first base 220, first cap 222, first teeth 224 and first fastener 226, and first lamellar spring 262 (FIG. 4). Second module 204 can comprise second base 228, second cap 230, second teeth 232 and second fastener 234. Shaft 206 can comprise outer barrel 235 in which main body 236 (FIG. 4) can be disposed. Main body 236 can comprise first coupler 238, second coupler 240, flange 242 and fastener 244.

First module 202 and second module 204 can comprise devices for holding an instrument, such as medical instruments including catheters, cannulas and guidewires. First module 202 and second module 204 can comprise adjustable jaws having teeth that can be retracted away from a center axis to adjust the width or diameter of passage 208. The jaws can be biased, such as is described with respect to FIGS. 5-9. However, the jaws can also not be biased, such as is described with reference to FIGS. 10-14. In the illustrated example, first module 202 is biased and second module 204 is not biased.

Mounting plate 214 can be mounted to robotic arm 120 (FIG. 2) such as by inserting threaded fasteners into bores 246. Extension 212 can be coupled to mounting plate 214 to provide a mounting arm for coupling with instrument holder 200. Extension 212 can include seat 248 having a semi-circular or circular arc length shape to receive and mate with main body 236 of shaft 206. Extension 212 and main body 236 can be coupled using any suitable means, such as fasteners or metallurgical bonding. Extension 212 can extend along an axis that is perpendicular to axis 210. Extension 212 is configured to align passage 208 extending through outer barrel 235 and main body 236 at a known position relative to bores 246 such that the position of passage 208 to robotic arm 120 is in a known, e.g., known to computing system 140, orientation. Thus, as robotic arm 120 moves instrument holder 200, the position of instrument holder 200 relative to surgical area 105 (FIG. 1) will also be known.

After instrument holder 200 is attached to robotic arm (FIG. 2) via mounting plate 214, second module 204 can be opened to a widened diameter to not obstruct passage 208, such as by rotating second cap 230. In the described examples, first module 202 can be biased to a closed position by a biasing mechanism described herein. However, in other examples first module 202 could be biased to an open position. The size of the opening of first module 202 can be adjusted by rotating first cap 222 and simultaneously inserting instrument 218 into passage 208. Releasing of first cap 222 will release the biasing mechanism to reposition the adjustable jaw formed by teeth 224 therein to close teeth 224 around instrument 218. Thereafter, first cap 222 can be manually rotated to move teeth 232 around instrument 218. Fasteners 226 and 234 can be adjusted to lock caps 222 and 230 in place, thereby immobilizing teeth 224 and 232. The use of two adjustable jaws around instrument 218 facilitates alignment of instrument 218 along axis 210 (FIG. 2) due to providing two reference points along axis 210 formed by each adjustable jaw. Fastener 244 can be adjusted to immobilize main body 236 within outer barrel 235. For example, threaded shaft 250 of fastener 244 could be rotated in bore 252 via head 254 to extend into outer barrel 235 and hold main body 236 concentrically within outer barrel 235. In additional examples, threaded shaft 250 can extend through main body 236 into passage 208 and engage instrument 218.

With reference to FIG. 4, instrument holder 200 can be assembled by attaching first coupler 238 to main body 236. Second coupler 240 can be integral with main body 236. First base 220 can be attached to first coupler 238, such as via threaded engagement. For example, external thread on first coupler 238 can engage internal thread 256 (FIG. 7) on first base 220. Second base 228 can be attached to second coupler 240, such as via threaded engagement. For example, external thread on second coupler 240 can engage internal thread on bore 258 of second base 228.

Teeth 224 can be positioned in first slots 260 of first base 220. Teeth 224 can be positioned to engage biasing elements 262 with the interaction of first cap 222, through its designated pins 306A, 306B and 306C. Teeth 232 can be positioned in second slots 264. First cap 222 can be coupled to first base 220 to secure and position the teeth 224 in equal radial fashion to provide the symmetry condition/synchronization of teeth 224. Second cap 230 can be coupled to second base 228 to secure teeth 232. First fastener 226 can be coupled to first base 220 to secure first cap 222. Second fastener 234 can be coupled to second base 228 to secure second cap 230 using slots 304A, 304B, 304C to maintain the synchronization condition.

Teeth 224 and 232 can be moved closer to and further away from axis 210 to close and open passage 208, thereby facilitating engagement with different sized instruments. Caps 222 and 230 can be manipulated by a surgeon or technician to adjust the position of teeth 224 and 232, respectively. Teeth 224 and 232 provide multiple contact points spaced axially apart along the instrument to provide stability and alignment on the instrument with axis 210. Further, teeth 224 and 232 can have axial length to further provide stability and alignment to the instrument. As shown in FIG. 4, components of instrument holder 200 can be disassembled for cleaning and sterilization for re-use with a subsequent medical procedure performed with robotic arm 120 (FIG. 2).

Figure 5:
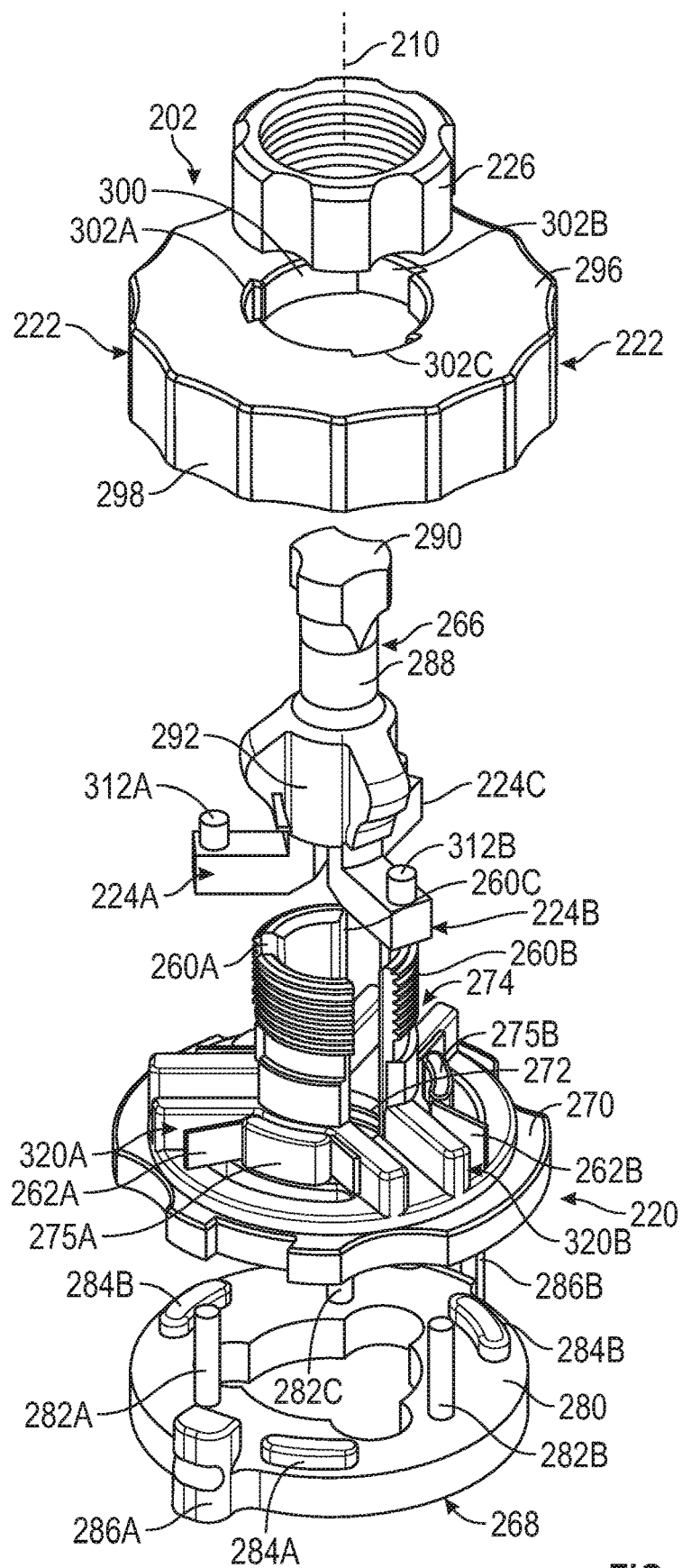
FIG. 5 is a perspective, partially-exploded view of the first module of FIG. 4 along with a tooth holder and a tensioner tool.

FIG. 5 is a perspective, partially-exploded view of first module 202 of FIG. 4 along with tooth holder 266 and tensioner tool 268. As described herein, first module 202 can be adjusted to hold an instrument of a given size. Tooth holder 266 and tensioner tool 268 comprise tools used in the assembly of first module 202, which are ultimately removed before use of first module 202. Tooth holder 266 can be used to hold first teeth 224A-224C as a unit for insertion of first teeth 224A-22C into slots 260A-260C of first base 220. Tensioner tool 268 can be used to retract biasing elements 262A-262C within spaces 320A-320C to a position where cap 22 will fit over teeth 224A-224C by making enough space for pins 306A-306C to fit within spaces 320A-320C (e.g. biasing elements 262A-262C should be kept in constant tension against pins 306A-306C during use in surgery and not in assembly). Before mounting cap 222, tensioner tool 268 can be turned in counterclockwise direction and pressed against two guides 286A and 286B to press against biasing elements 262A-262C. After cap 222 is positioned correctly over first base 220, the two guides can be released and both tensioner tool 268 and tooth holder 266 can be removed. After teeth 224A-224C are inserted, tooth holder 266 can be removed from teeth 224A-224C and tensioner tool 268 can be removed from first base 220.

Figure 6:
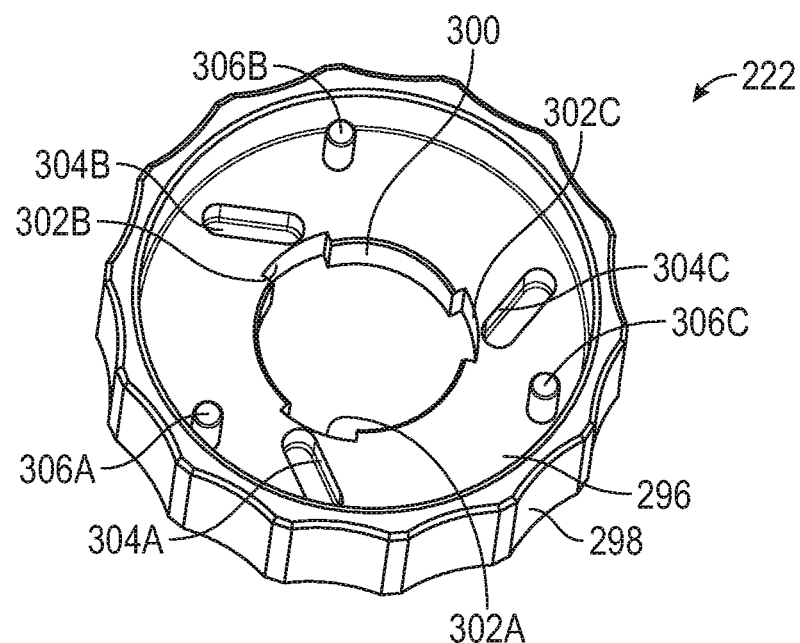
FIG. 6 is a schematic illustration showing perspective top views of a base of the first module and the tensioner tool and a perspective bottom view of a cap of the first module.
Figure 6:
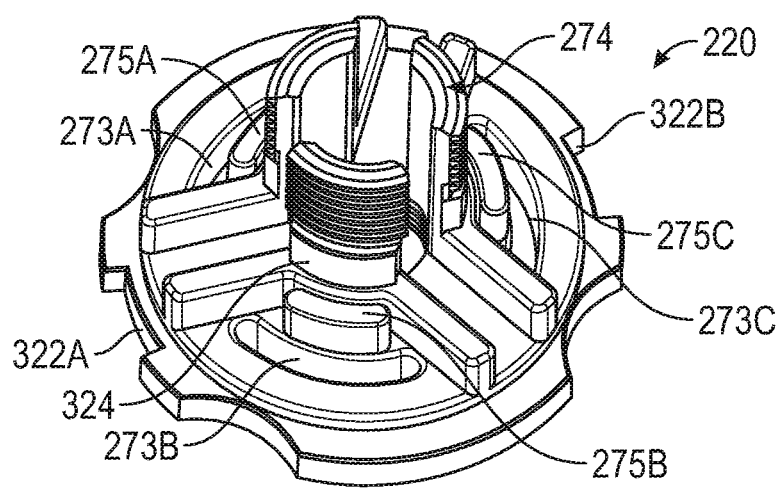
Figure 6:
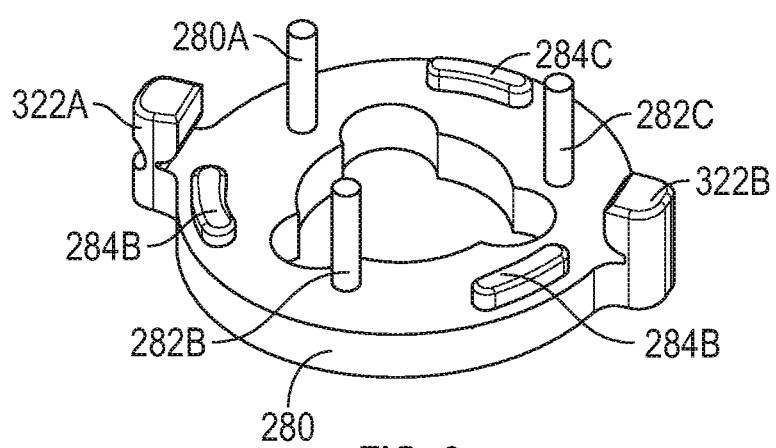
Figure 7:
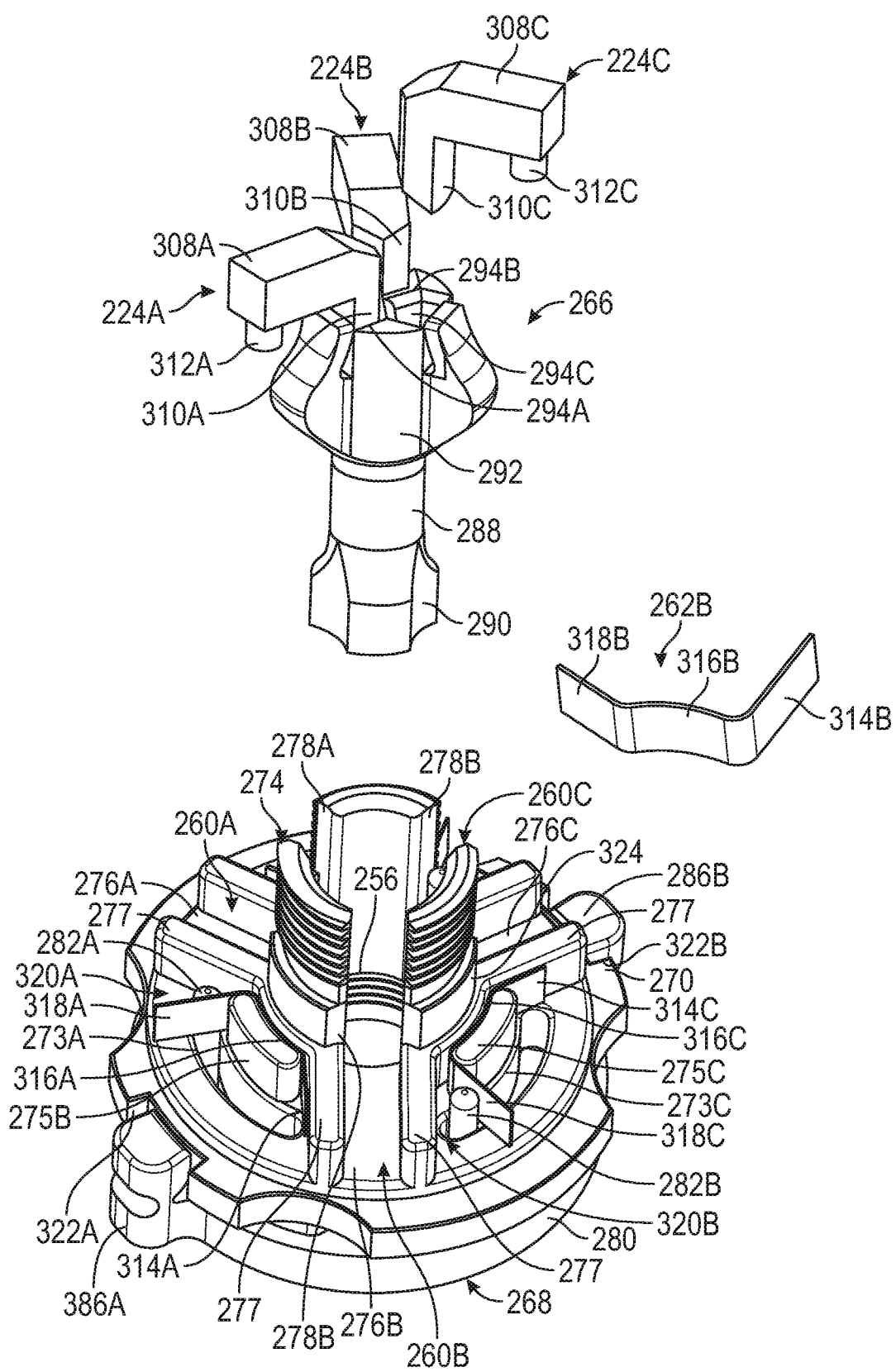
FIG. 7 is a perspective view of a partially assembled first module showing biasing elements engaged with posts of the tensioner tool and teeth positioned proximate the tooth holder.

First module 202 can comprise first base 220, first cap 222, first teeth 224A-224C, first fastener 226 and biasing elements 262A-262C. FIG. 6 is a schematic illustration showing perspective top views of base 220 of first module 202 and tensioner tool 268 and a perspective bottom view of cap 222 of first module 202. FIG. 7 is a perspective view of partially assembled first module 202 showing biasing elements 262A-262C engaged with posts 282A-282C of tensioner tool 268 and teeth 224A-224C positioned proximate tooth holder 266. In order to understand the assembly and operation of the various components and features of instrument holder 200, FIGS. 5-7 are discussed concurrently.

First base 220 can comprise first disk 270 having first bore 272, first channels 273A-273C, first post 274, first guide slots 260A-260C and pedestals 275A-275C. Slot 260A can comprise disk portion 276A and post portion 278A; slot 260B can comprise disk portion 276B and post portion 278B; and slot 260C can comprise disk portion 276C and post portion 278C. Disk portions 276A-276C can be formed via flanges or walls 277 extending from first disk 270. Post portions 278A-278C can be formed via slots or gaps in first post 274.

Tensioner tool 268 can comprise platform 280, posts 282A-282C, pads 284A-284C and guides 286A-286B. Tension tool 268 can comprise a device to pre-tension or otherwise move biasing elements 262A-262C to facilitate positioning of teeth 224A-224C into slots 260A-260C. Before mounting cap 222, tensioner tool 268 can be turned in counterclockwise direction and pressed against two guides 286A and 286B to press against biasing elements 262A-262C.

After cap 222 is positioned correctly over first base 220, the two guides can be released and both tensioner tool 268 and tooth holder 266 can be removed.

Tooth holder 266 can comprise handle shaft 288, knob 290 and socket portion 292. As can be seen in FIG. 6, socket portion 292 can include sockets 294A, 294B and 294C. Socket portion 292 can comprise a cartridge for holding teeth 224A-224C together as a unit in a pre-arranged configuration commensurate with the shape of slots 260A-260C.

First cap 222 can comprise top panel 296, sidewall 298, aperture 300 and cut-outs 302A-302C. As can be seen in FIG. 6, first cap 222 can further comprise positioning slots 304A-304C and pegs 306A-306C.

Tooth 224A can comprise rail 308A, spoke 310A and tab 312A; tooth 224B can comprise rail 308B, spoke 310B and tab 312B; and tooth 224C can comprise rail 308C, spoke 310C and tab 312C.

As can be seen in FIG. 7, biasing elements 262A-262C can comprise resilient members configured to deflect and absorb energy from a force and then return to their original shape after the force has been removed. In an example, biasing elements 262A-262C can comprise lamellar spring elements. For example, biasing elements 262A-262C can comprise rectangular strips of a resilient material, such as metal, that can be bent into three sections. In an example, biasing element 262A can comprise straight first section 314A, curved second section 316A and straight third section 318A; biasing element 262B can comprise straight first section 314B, curved second section 316B and straight third section 318B; and biasing element 262C can comprise straight first section 314C, curved second section 316C and straight third section 318C.

In order to assemble first module 202, biasing elements 262A-262C can be assembled to first base 220 first. For example, curved second section 316A can be positioned between first post 274 and first pedestal 275A so that straight first section 314A is positioned against one of walls 277. Thus, straight second section 316A can be spaced an amount from another of walls 277 to form gap 320A. Posts 282A of tensioner device can be inserted into space 320A. Likewise, biasing elements 262B and 262C can be positioned in base 220 and engaged with posts 282B and 282C, respectively, in spaces 320B and 320C.

Tensioner tool 268 can be positioned underneath first base 220 such that posts 282A-282C align with channels 273A-273C, respectively. Platform 280 can be pushed towards first base 220 until pads 284A-284C engage the bottom of disk 270. In such a position, guides 286A and 286B can engage the side of disk 270 to facilitate rotation of platform 280 relative to disk 270 and posts 282A-282C can be positioned within spaces 320A-320C, respectively. Guides 286A and 286B can be positioned within cut-outs 322A and 322B, respectively, to prevent relative movement between disk 270 and platform 280. With tensioner tool 268 locked into place via guides 286A and 286B, spaces 320A-320C can be held in an enlarged state while posts 282A-282C hold biasing elements 262A-262C.

Teeth 224A-224C can be positioned within slots 260A-260C, respectively, of tooth holder 266. Teeth 224A-224C can be assembled into first base 220 using tooth holder 266. Specifically, as shown in FIG. 7, spokes 310A-310C can be inserted into sockets 294A-294C, respectively. Spokes 310A-310C can be pentagon shaped with two parallels sides such that two other sides form an apex pointing toward axis 210. The apex can be rounded to engage the surgical instrument. Sockets 294A-294C can be correspondingly shaped and correspondingly sized such that spokes 310A-310C can be freely inserted but retained. As such, tooth holder 266 can be grasped at knob 290 and orientated to the position of FIG. 7 for loading of teeth 224A-224C into tooth holder 266 and the reoriented to the position of FIG. 5 for insertion of teeth 224A-224C into slots 260A-260C, respectively. From the position of FIG. 5, tooth holder 266 can be advanced toward base 220 to position rails 308A-308C into disk portions 276A-276C of slots 260A-260C and spokes 310A-310C into post portions 278A-278C of slots 260A-260C. Thus, spokes 310A-310B can be sandwiched between portions of post 274 and rails 308A-308C can be sandwiched between two adjacent walls 277. Positioned as such, teeth 224A-224C can freely slide in slots 260A-260C to move toward and away from axis 210. Teeth 224A-224C can be slid toward axis 210 to contact each other in order to constrict passage 208. The apex of spokes 310A-310B can be rounded to provide a minimum diameter for passage 208. Teeth 224A-224C can be retracted away from axis 210 until rails 308A-308C contact sidewall 298 of cap 222 to thereby open passage 208. Movement of teeth 224A-224C can be controlled by rotation of cap 222 and engagement of tabs 312A-312C with 304A-304C, respectively.

First cap 222 can be assembled to first base 220 by positioning first post 274 into aperture 300. Aperture 300 can be un-threaded such that first cap 222 can freely rotate about first post 274 at shoulder 324. As can be seen in FIG. 6, cap 222 can include slots 304A-304C and pegs 306A-306C for engagement with biasing elements 262A-262C and teeth 224A-224C, respectively. Each of slots 304A-304C can comprise a straight segment extending at a forty-five-degree angle relative to a radial direction extending from axis 210 (FIG. 2) Cap 222 can be rotated back-and-forth to position pegs 306A-306C into spaces 320A-320C, respectively, and slots 304A-304C can receive tabs 312A-312C, respectively. Cut-outs 302A-302C can be aligned with slots 260A-260C to facilitate positioning of cap 222 around tooth holder 266, tooth holder 266 can subsequently be removed from engagement with teeth 224A-224C, and fastener 226 can be positioned around post 274 to secure cap 222 to base 220, as is shown in FIG. 8.

Figure 8:
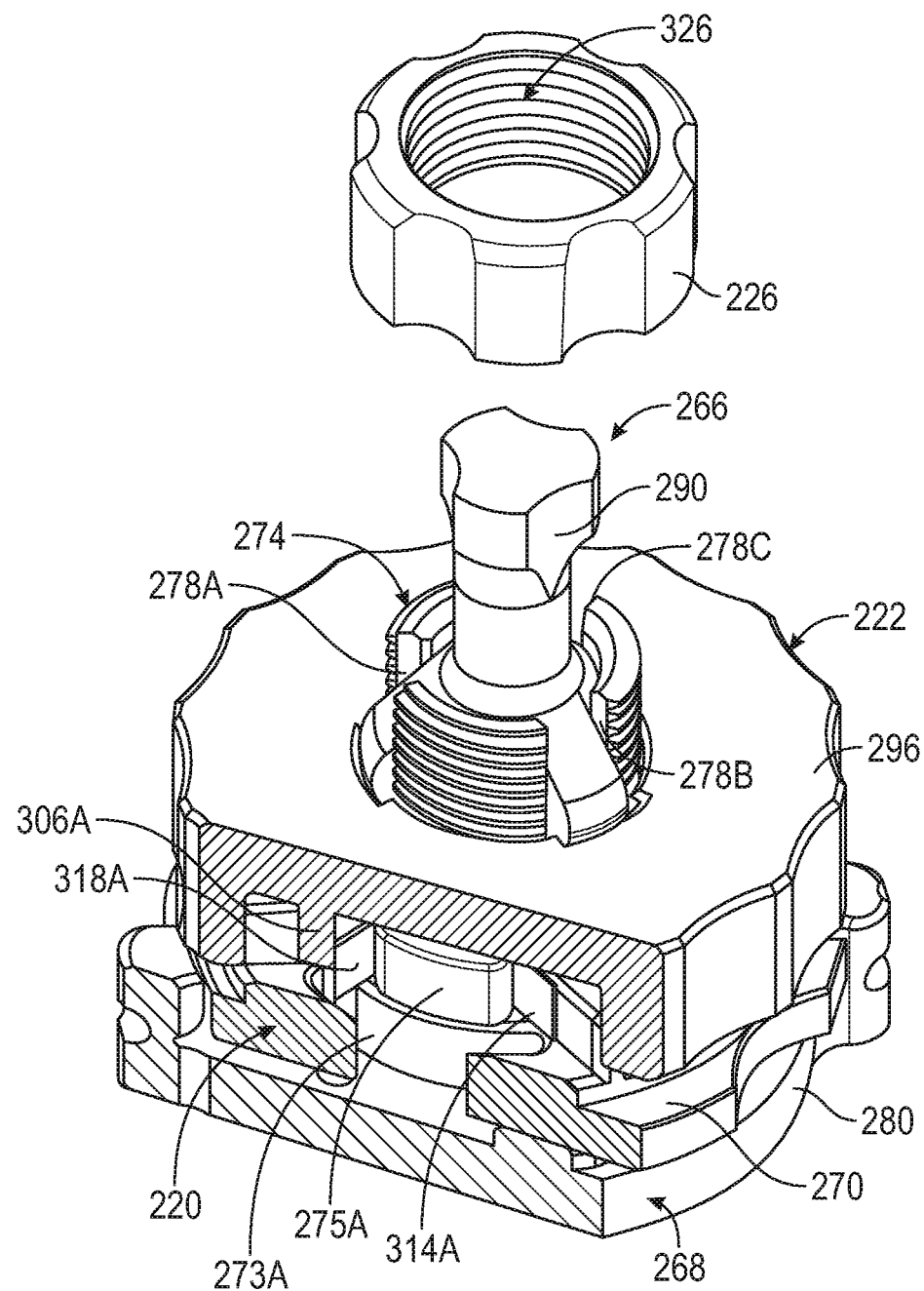
FIG. 8 is a partially exploded and cut-away view of the assembled first module together with the tensioner tool, the tooth holder, a cap and a fastener.

FIG. 8 is a partially exploded and cut-away view of assembled first module 202 together with tensioner tool 268 and tooth holder 266. Fastener 226 is positioned to receive post 274 of base 220, after tooth holder 266 is removed from teeth 224A-224C. Fastener 226 can comprise socket 326 to which post 274 can be coupled, such as via threaded engagement. Socket 326 can include internal threading that can receive external threading on the exterior of post 274. As can be seen in FIG. 8, peg 306A can be positioned to engage straight third section 318A of biasing element 262A.

Figure 9:
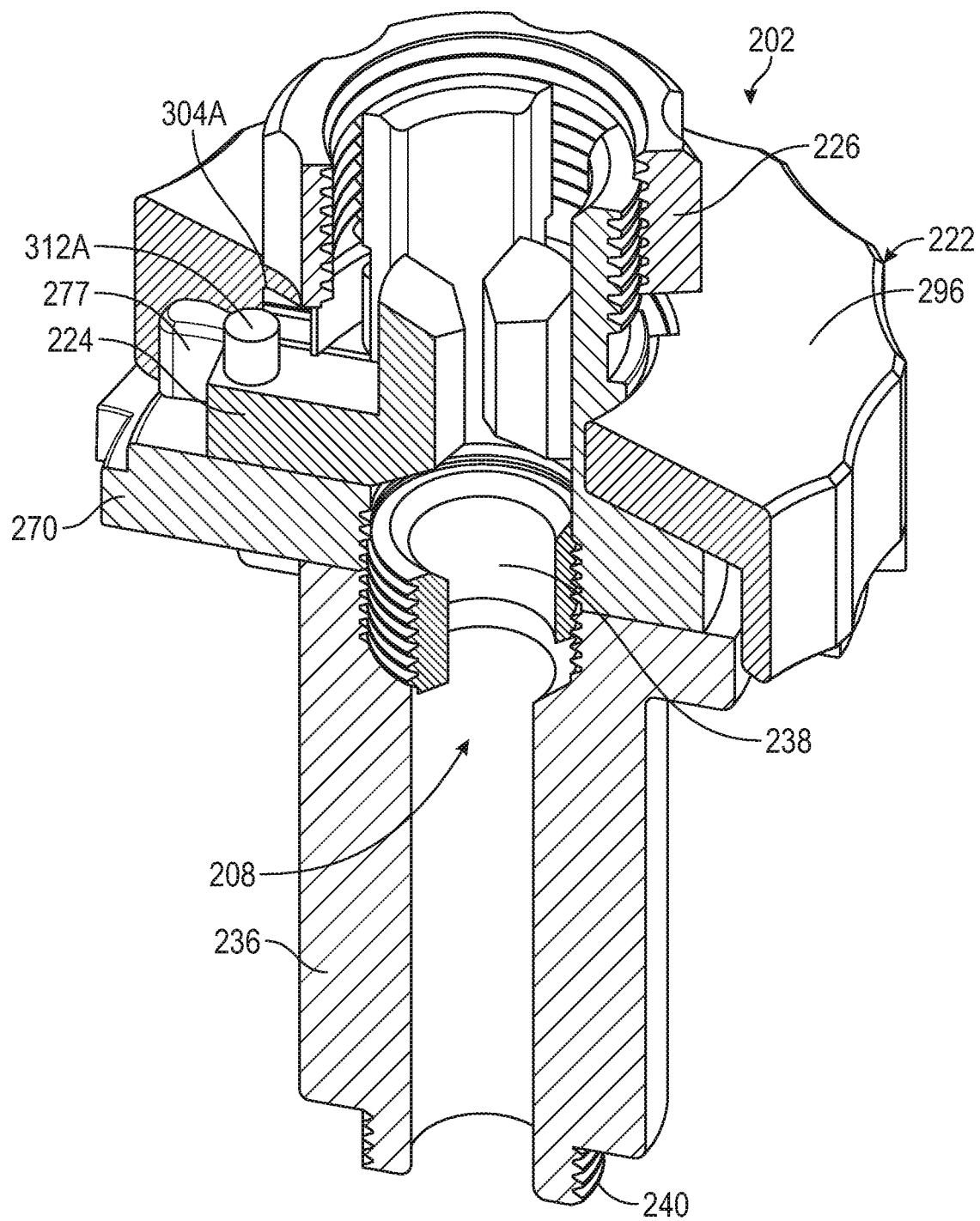
FIG. 9 is a sectioned perspective view of the first module of FIG. 8 assembled with the main shaft and the tensioner tool and tooth holder removed.

FIG. 9 is a sectioned perspective view of the first module 202 assembled with shaft 206. Cap 222 can be rotated counter-clockwise to move teeth 224A-224C away from axis 210 and clockwise to move teeth 224A-224C toward axis 210, as tabs 312A-312C are driven by sidewalls of slots 304A-304C. Biasing elements 262A-262C can be used to rotate cap 222 in a clockwise direction to move teeth 224A-224C to an inward position to constrict around an instrument, so a user does not have to do it. For example, the user can rotate cap 222 in a counter-clockwise direction, insert instrument 218 and then releases cap 222 to hold the instrument. Cap 222 can rotate by itself in clockwise direction via biasing elements 232A-232C. To secure that position, for accidental position deviations from axis 210 during use, fastener 226 can be used. Additionally, the user can rotate cap 222 in a clockwise direction to move teeth 224A-224C to an inward position to constrict around an instrument. While holding cap 222 in a desired position, fastener 226 can be tightened down on post 274 to push cap 222 against walls 277 of base 220. Thus, biasing elements 262A-262C will be constrained from moving teeth 224A-224C and passage 208 can be held at a fixed size to guide the instrument. Biasing elements 262A-262C can give enough force to the teeth 224A-224C to hold any instrument to prevent falling, and thus offering more ease during use for other hand manipulations. In order to remove an instrument or reset first module 202 to a fully open position, fastener 226 can be rotated to move away from cap 222 so that module 202 can be opened, such as by applying a user-generated force to cap 222 in a counter-clockwise direction so that teeth 224A-224C can be opened, overcoming force form biasing elements 262A-262C.

As mentioned, in other examples, biasing elements 262A-262C can bias cap 222 in the counter-clockwise direction to bias teeth 224A-224C away from each other. In such a configuration, first module 202 will bias to an open position, thereby facilitating one-handed release.

As such, first module 202 provides an adjustable instrument holding or guiding device that can be disassembled for cleaning and sterilization. Peripheral devices 266 and 268 can be used to easily re-assemble and disassemble first module 202. Once assembled, cap 222 can be rotated to a desired position to facilitate guiding of instruments having different sizes or diameters.

Figure 10:
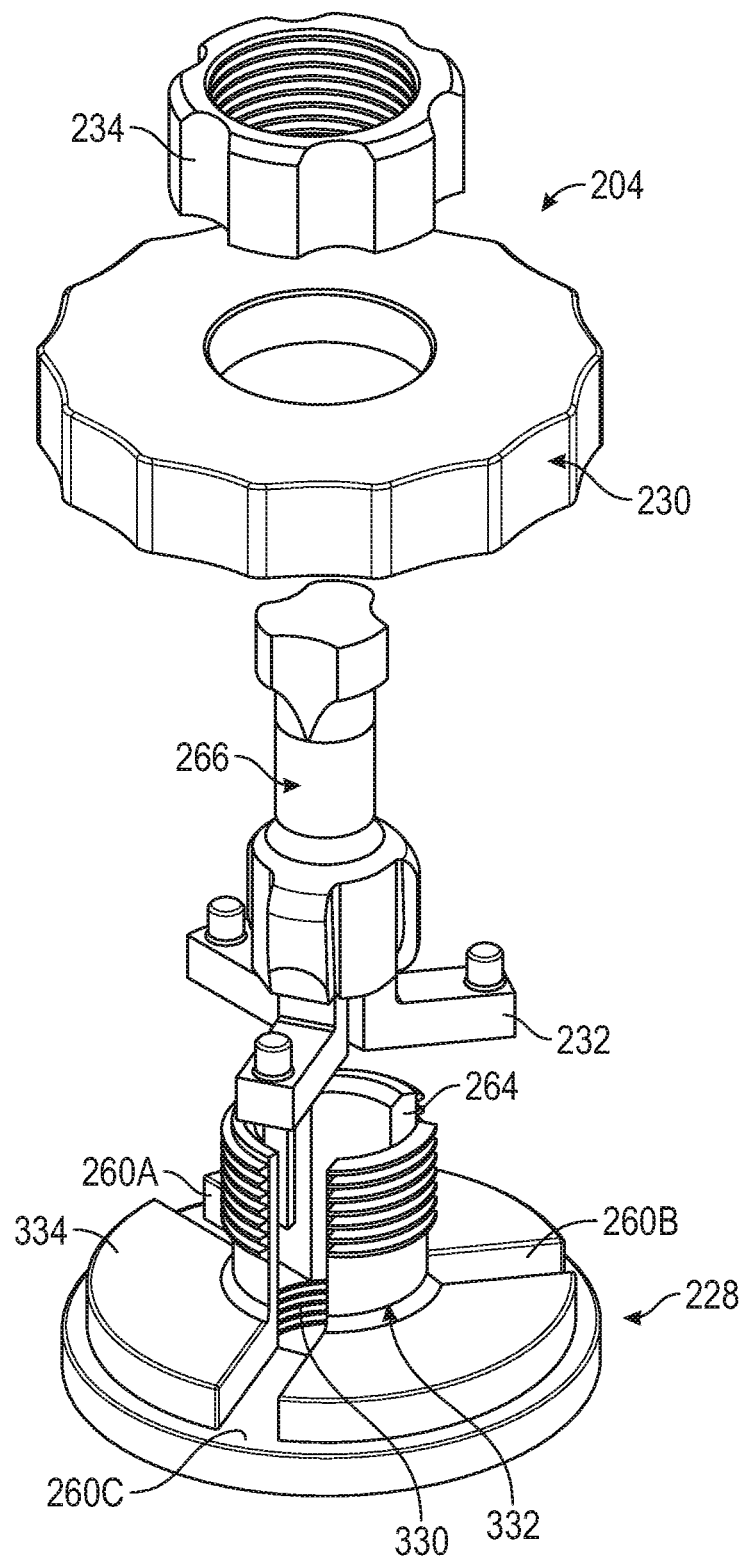
FIG. 10 is a perspective view of the second module of FIG. 3 showing a base, a plurality of teeth coupled to a tooth holder, a cap and a fastener.

FIG. 10 is a perspective view of second module 204 of FIG. 4 showing base 228, teeth 232 coupled to tooth holder 266, cap 230 and fastener 234. Note, tooth holder 266 as depicted in FIG. 10 has a slightly different geometry than tooth holder 266 depicted in FIG. 7 (the three outer projections help the correct assembly of cap 222 through cut-outs 302A-302C as a fool-proof system, whereas the tooth holder 226 in FIG. 10 holds teeth 232A-232C equidistant while cap 230 is continuously rotated against the tooth holder until it is positioned correctly). Second module 204 can be configured similarly as first module 202, but without biasing elements 262A-262C. Thus, the construction of base 228 can be simplified as compared to base 220. For example, channels 273A-273C and pedestals 275A-275C can be omitted, as coupling with tensioner tool 268 and securing of biasing elements 262A-262C is not needed. Fastener 234 can be configured similarly as fastener 226.

Figure 11:
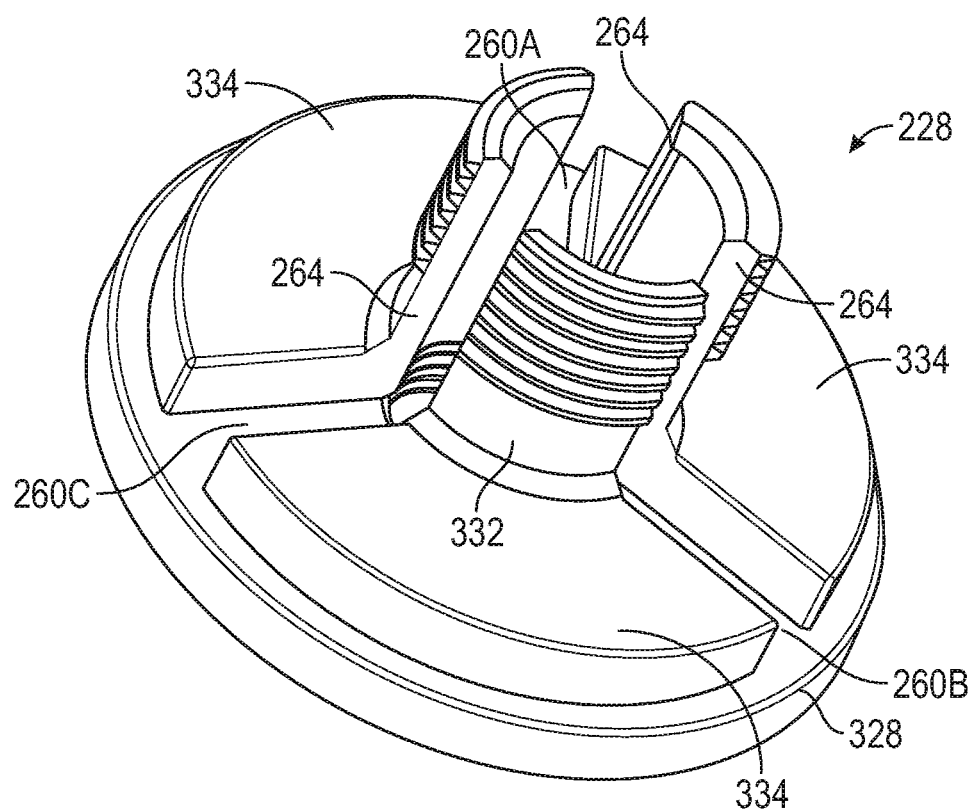
FIG. 11 is a perspective view of a top or outside of the base of FIG. 10 showing slots for the teeth.

FIG. 11 is a perspective view of top or outside of base 228 of FIG. 10 showing slots 260A-260C for teeth 232A-232C. Second base 228 can comprise second disk 328 having second bore 330, slots 260A-260C, second post 332 and pads 334A-334C. Pads 334A-334C can form sidewalls for forming disk portions of slots 260A-260C and second post 332 can include cut-outs or slots for forming post portions of slots 262A-262C. Second bore 330 can be threaded for mating with second coupler 240. Teeth 232A-232C can be configured similarly as teeth 224A-224C.

Figure 12:
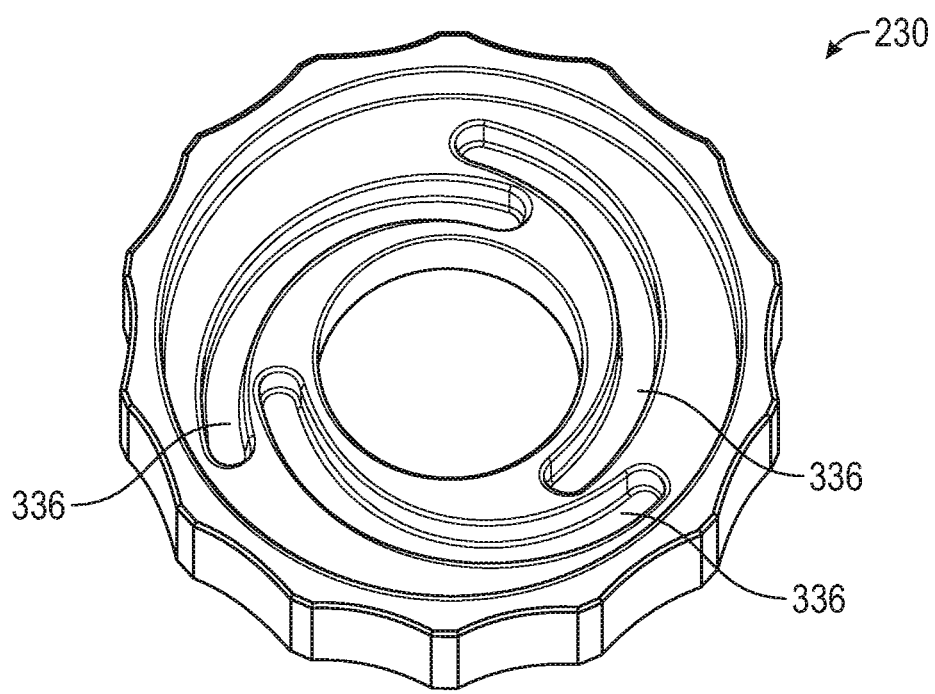
FIG. 12 is a perspective view of a bottom or inside of the cap of FIG. 10 showing arcuate adjustment slots for guiding movement of the teeth.

FIG. 12 is a perspective view of the bottom or inside of cap 230 of FIG. 10 showing arcuate adjustment slots 336A-336C for guiding movement of teeth 232A-232C. Cap 230 can be configured similarly as cap 222, but without cut-outs 302A-302C and pegs 306A-306C. Pegs 306A-306C are not needed because interaction with biasing elements 262A-262C is not needed. Cut-outs 302A-302C are not needed because it is not necessary for cap 230 to be particularly aligned so that pegs 306A-306C align with spaces 320A-320C. Furthermore, since the presence of pegs 306A-306C is not required, slots 336A-336C can be longer than slots 304A-304C. Each of slots 336A-336C can comprise a circular arc segment having a radius of curvature center eccentric with axis 210 (FIG. 2). As such the stroke-length of cap 230 can be increased as compared to that of cap 222. In other words, a larger rotation of cap 230 will be produce the same amount of movement of teeth 232 as a smaller rotation of cap 222 will produce for teeth 224. For example, full movement of teeth 232 can be produced with a one-third turn, whereas full movement of teeth 224 with cap 222 can be produced with a one-ninth turn. The longer stroke length provides an operator the ability of small and more precise/ fine adjustment if needed, or a faster interaction with the device as first module.

Figure 13A:
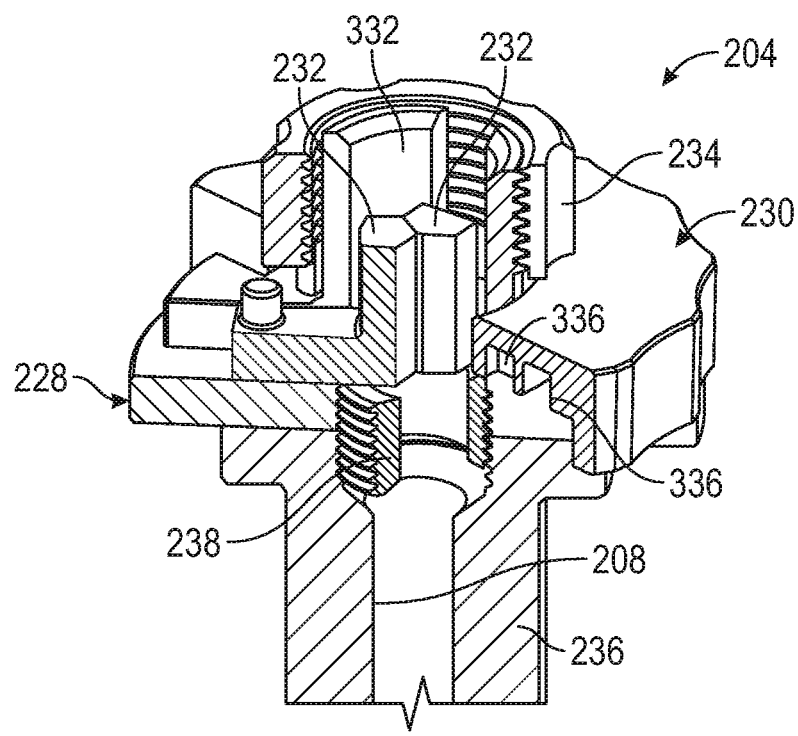
FIG. 13A is a sectioned perspective view of the second module of FIG. 10 in an assembled state with the teeth in a closed position.
Figure 13B:
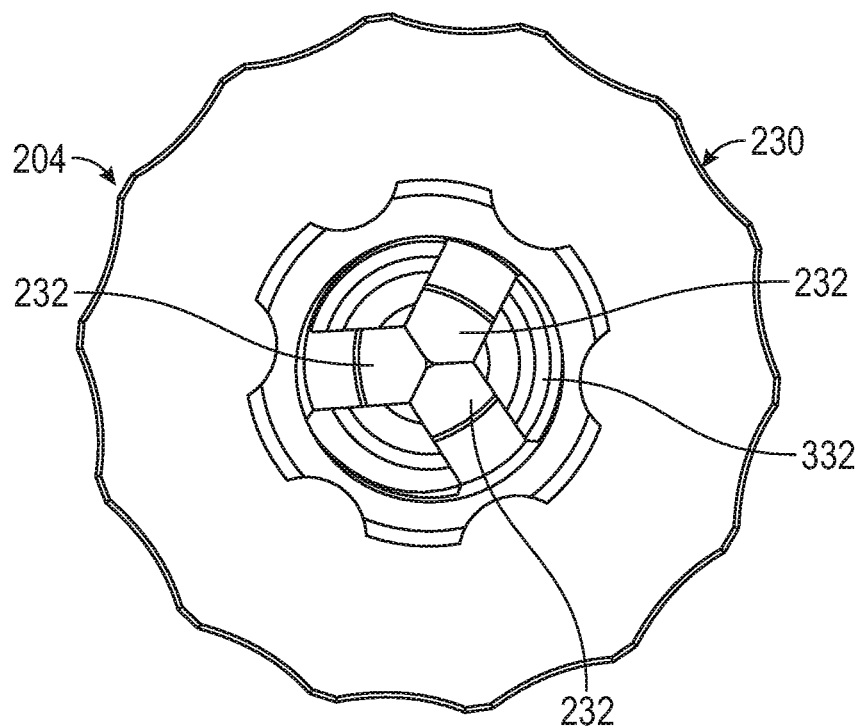
FIG. 13B is a top view of the second module of FIG. 13A showing contact of the teeth with each other.

FIG. 13A is a sectioned perspective view of second module 204 of FIG. 10 in an assembled state with teeth 232 in a closed position. FIG. 13B is a top view of second module 204 of FIG. 13A showing contact of teeth 232 with each other. However, as discussed above, the radially inner tips of spokes 310A-310C that face toward axis 210 can be blunted or rounded to provide a minimum diameter for passage 208 even when teeth 232 are brought into contact with each other.

Figure 14A:
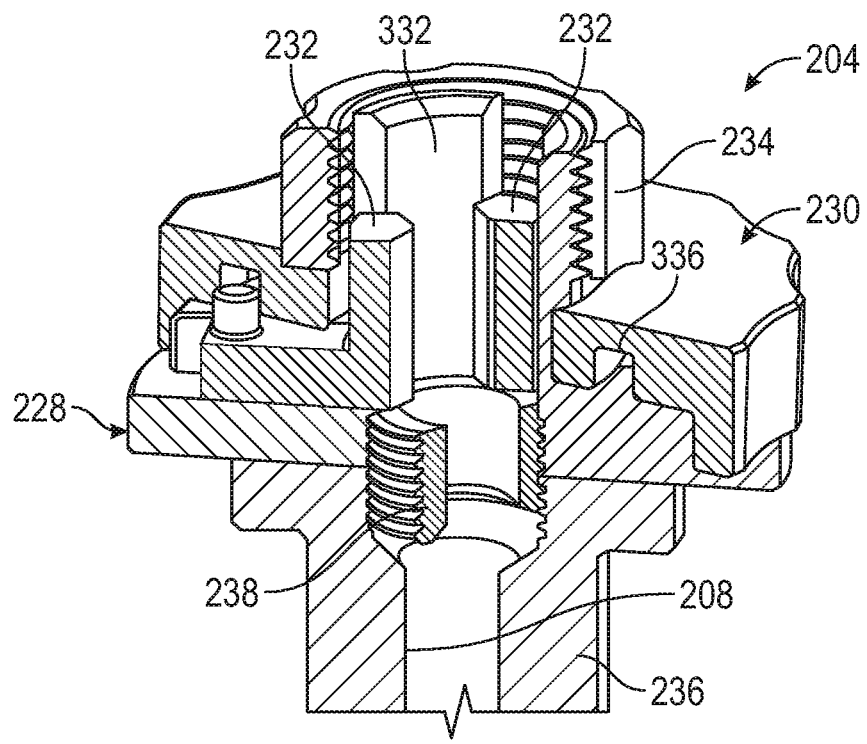
FIG. 14A is a sectioned perspective view of the second module of FIG. 10 in an assembled state with the teeth in an open position.
Figure 14B:
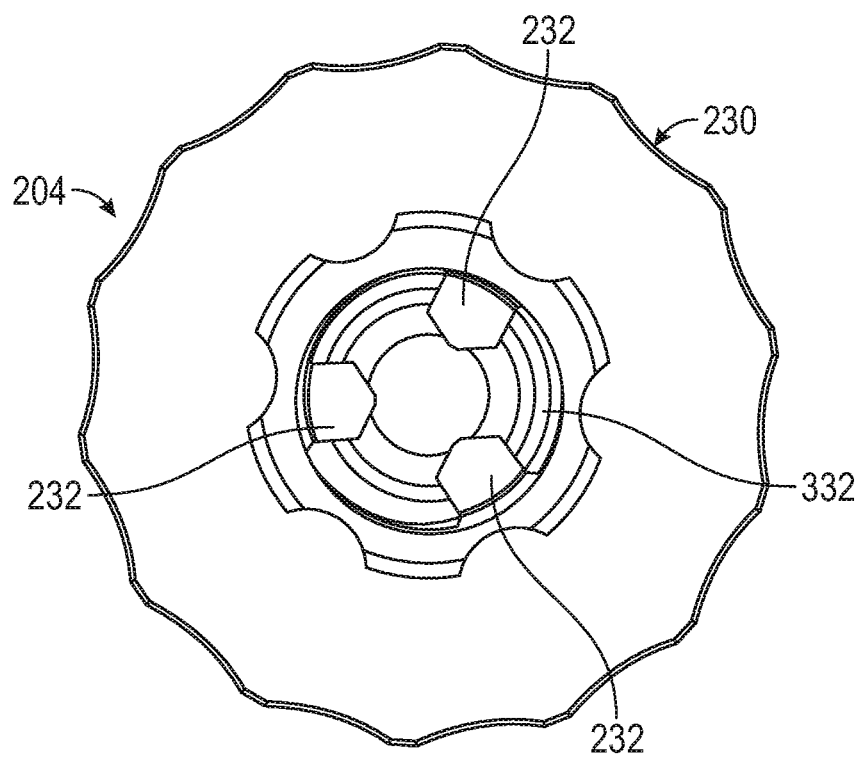
FIG. 14B is a top view of the second module of FIG. 14A showing the teeth moved away from each other to open a passage through the second module.

FIG. 14A is a sectioned perspective view of second module 204 of FIG. 10 in an assembled state with teeth 232 in an open position. FIG. 14B is a top view of second module 204 of FIG. 14A showing teeth 232 moved away from each other to open passage 208 through second module 204.

Figure 15:
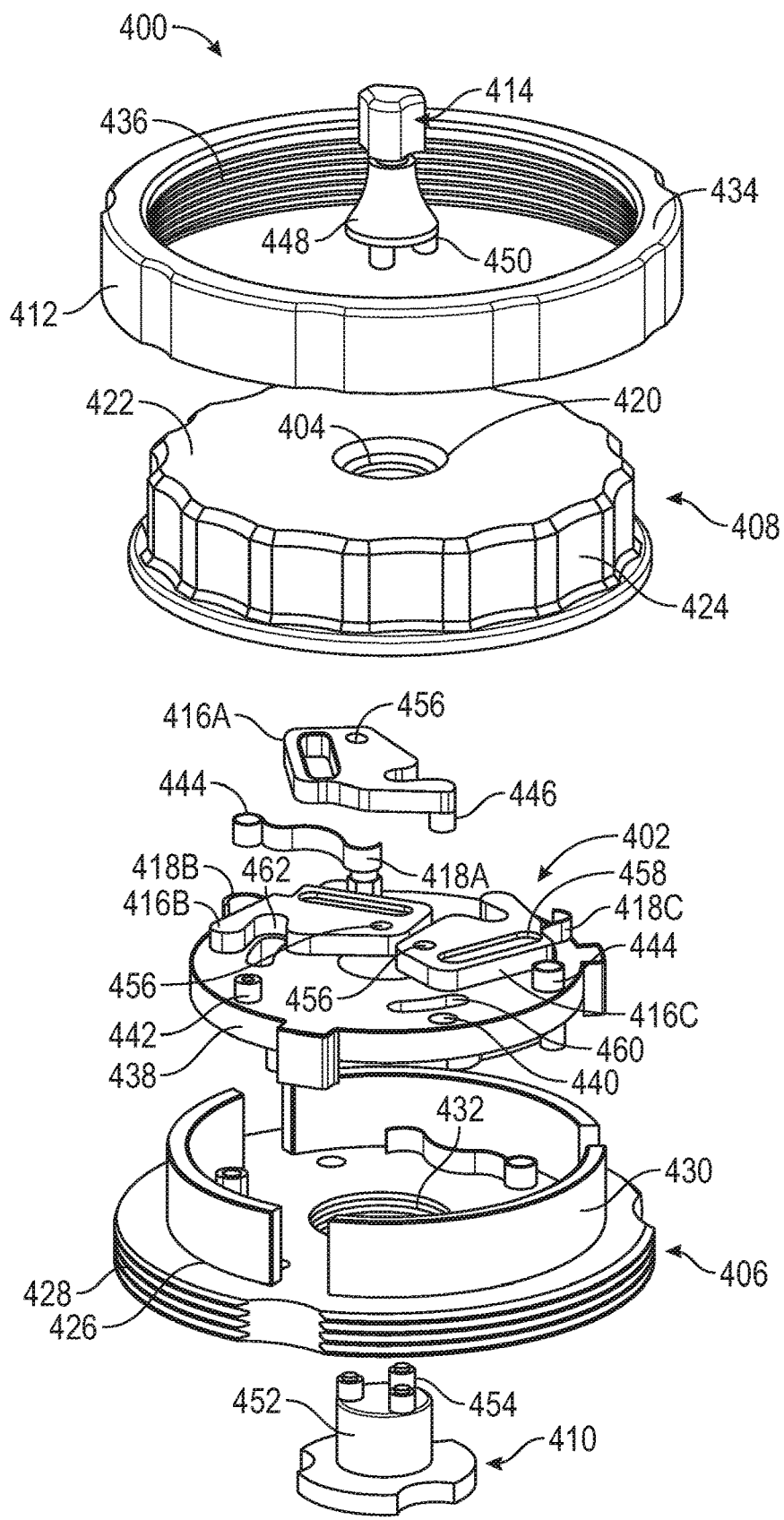
FIG. 15 is an exploded view of an alternative instrument holder module having a diaphragm to open and close a passage therethrough.
Figure 16:
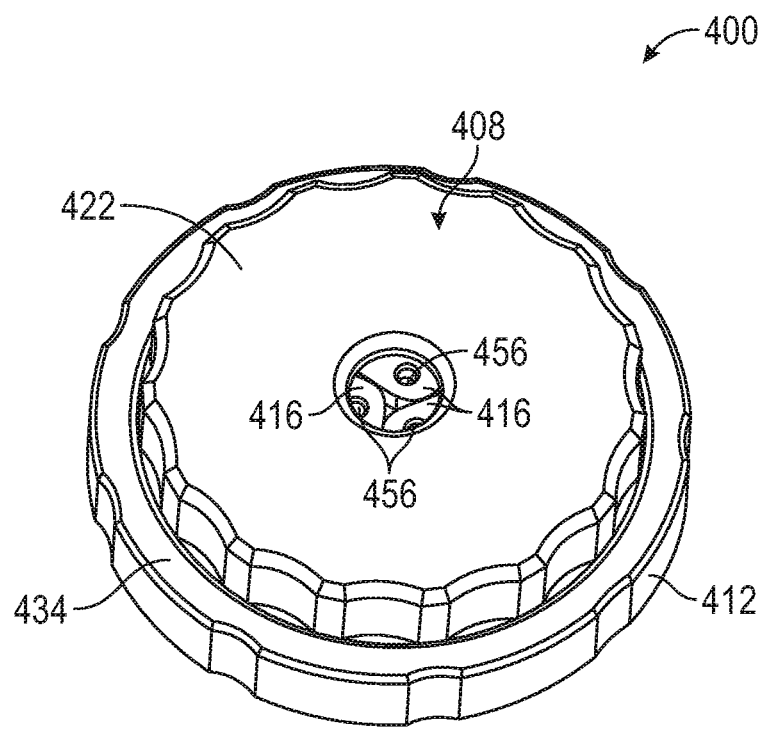
FIG. 16 is a perspective view of the alternative module of FIG. 15 in an assembled state showing three blades of the diaphragm obstructing a passage through a cap.

FIG. 15 is an exploded view of alternative module 400 where diaphragm 402 acts to open and close passage 404 therethrough. FIG. 16 is an assembled view of the alternative module of FIG. 15 showing blades 416A-416C closing passage 404 therethrough. Alternative module 400 can comprise base 406, cap 408, first blade locker 410, ring 412 and second blade locker 414. Diaphragm 402 can comprise blades 416A, 416B and 416C, and springs 418A, 418B and 418C.

Cap 408 can comprise aperture 420, lid 422 and sidewall 424. Base 406 can comprise base 426, threaded edge 428, guide walls 430 and aperture 432. Ring 412 can comprise lip 434 and threaded wall 436. Diaphragm 402 can be mounted onto platform 438, which can include bores 440 for coupling to blades 416A-416C and pegs 442 for coupling to springs 418A-418C. For example, springs 418A-418C can comprise sockets 444 for receiving pegs 442, and blades 416A-416C can include posts 446 for insertion into bores 440.

Second blade locker 414 can include shaft 448 and pegs 450. First blade locker 410 can include hub 452 and pegs 454. Blade lockers 414 and 410 can be used to adjust the position of blades 416A-416C via engagement of bores 456. Second blade locker 414 can be used to adjust diaphragm 402. First blade locker 410 can be used to adjust an additional diaphragm (not visible) mounted to the underside of platform 438. Blade lockers 414 and 410 can be mainly designed for and used in the assembly process. For the bottom side, blades 416A-416C can be placed on blade locker 410, having base 406 in between and aligned into place, the three springs on the bottom can be armed afterwards. Platform 438 will be then lowered and aligned to position. Use of blade locker 414 comes next, maintaining the same sequence as above, and further, cap 408 can be mounted over. To secure assembly alignment, the removal of the blade lockers 414 and 410 will only take place after ring 412 is inserted and secured.

Figure 17:
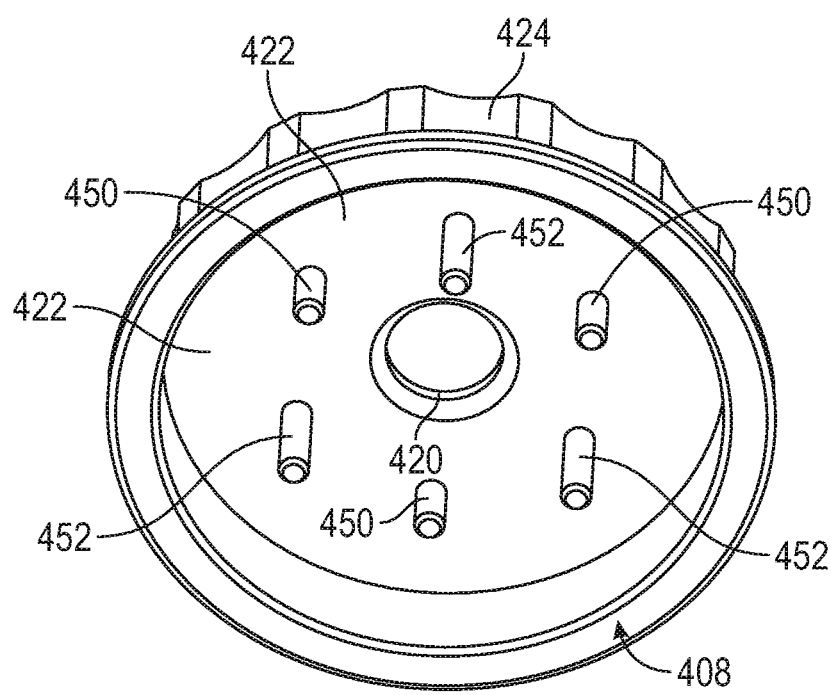
FIG. 17 is a perspective view of an underside of the cap of FIG. 16 for the alternative module showing prongs for moving the blades of the diaphragm.

Blades 416A-416C can further comprise slots 458 and platform 438 can comprise slots 460. As is shown in FIG. 17, cap 408 can include posts 450 and posts 452 for engaging slots of each diaphragm mechanism, respectively. Posts 450 can engage slots 458 of blades 416A-416C directly. Posts 452 can engage bores of the lower diaphragm after extending through slots 460.

FIG. 17 is a perspective view of an underside of cap 408 for alternative module 400 of FIGS. 15 and 16. Cap 408 can comprise posts 450 and posts 452. Posts 452 are longer than posts 450. Posts 450 can extend from lid 422 directly into slots 458. Cap 408 can be rotated to adjust the position of blades 416A-416C via engagement of posts 450 with slots 458. Blades 416A-416C can rotate on posts 446 in bores 440. Springs 418A-418C can bias blades 416A-416C to close in together within passage 404. Cap 408 can thus be rotated to move blades 416A-416C away from each other to open passage 404 for the insertion of an instrument therein. As blades 416A-416C rotate, slots 460 can allow posts 452 to extended through platform 438 to reach the blades of the additional diaphragm (not visible). Blades 416A-416C can include notches 462 to accommodate posts 452. Posts 452 can interact with blades of the additional diaphragm the same way that posts 450 interact with blades 416A-416C. Thus, cap 408 can be rotated to simultaneously open passage 404. Providing two levels of blades provides a lengthier, e.g., compared to having only own level of blades, path along which to guide an instrument. However, the instrument holders of the present application can be implemented with only a single level of blades, such as by having blades 416A-416C only. Once cap 408 is moved to the desired position to hold a specific instrument, ring 412 can be tightened down on base 406 by engagement of threaded wall 436 with threaded edge 428.

Figure 18:
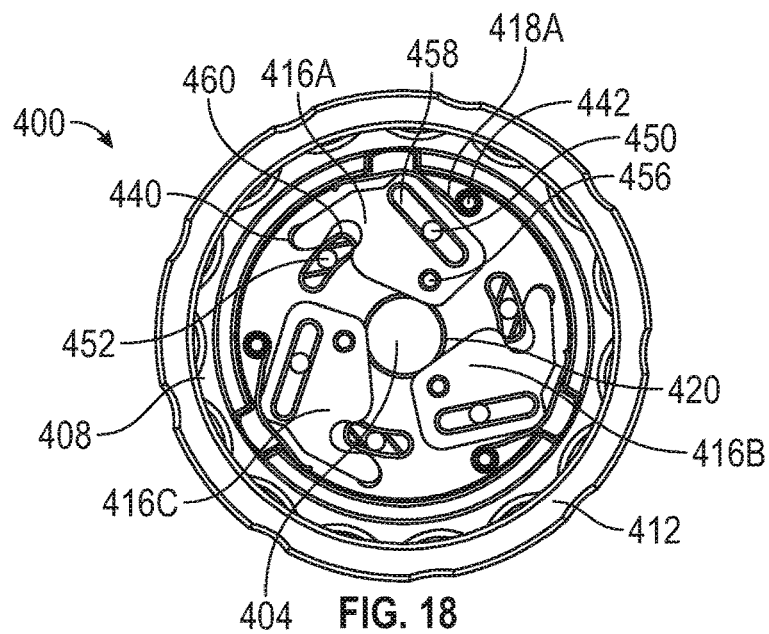
FIGS. 18-20 are top views of the alternative module of FIGS. 15-17 with the diaphragm in open, partially open and closed states, respectively.
Figure 19:
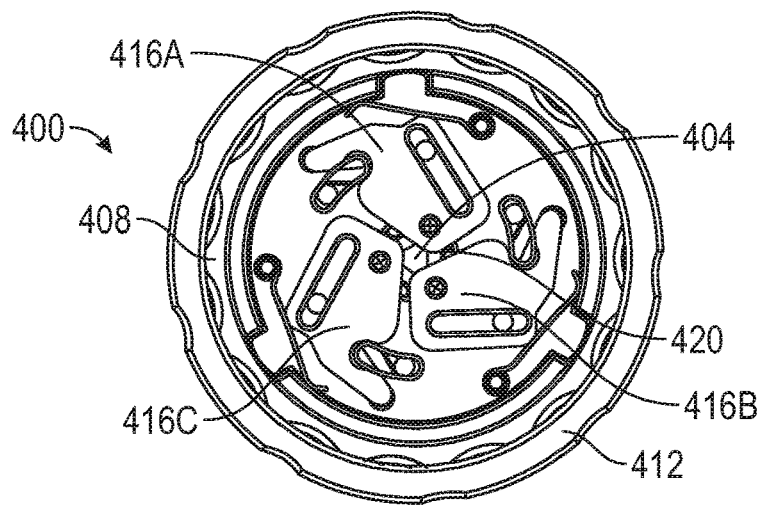
Figure 20:
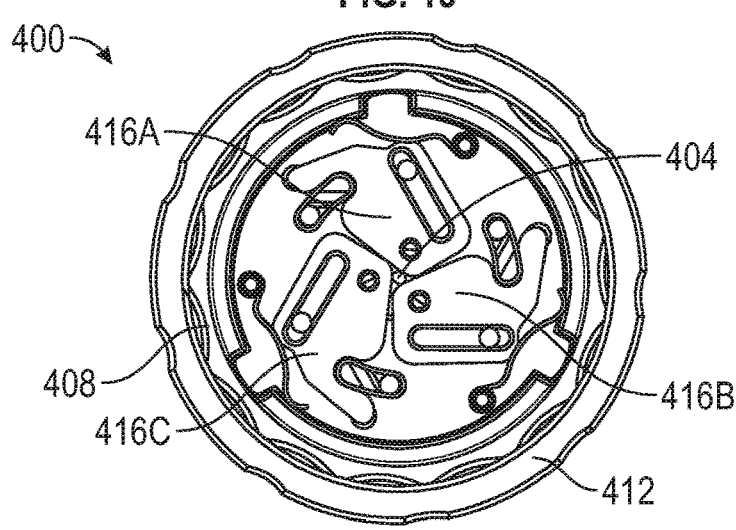

FIGS. 18-20 are top views of alternative module 400 of FIGS. 15 and 16 with diaphragm 402 in open, partially open and closed states, respectively. In FIG. 18, blades 416A-416C are shown fully retracted away from passage 404 and aperture 420 in cap 408. In FIG. 19, cap 408 can be rotated to move blades 416A-416C partially into passage 404. In FIG. 20, cap 408 can be further rotated in the clockwise direction to bring blades 416A-416C into close proximity to each other, thereby constricting the width of passage 404. A second layer of blades beneath blades 416A-416C can be seen in FIG. 20.

Figure 21:
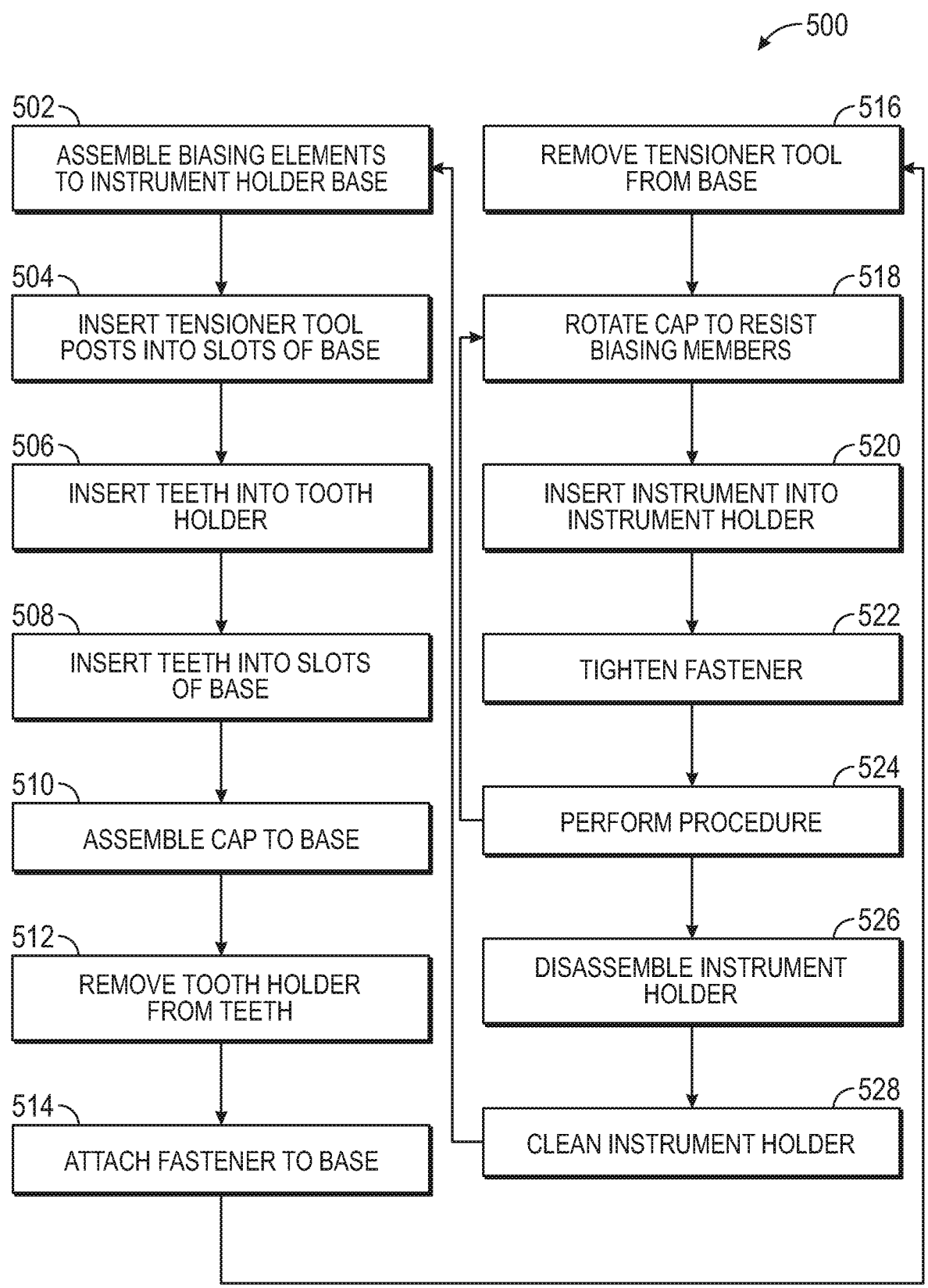
FIG. 21 is a flow chart illustrating steps of methods for assembling an instrument holder configured for use with a robotic surgical system, exchanging instruments mounted to the instrument holder and cleaning the instrument holder.

FIG. 21 is a flowchart illustrating actions or steps of methods or technique 500 for assembling an instrument holder configured for use with a robotic surgical system, exchanging instruments mounted to the instrument holder and cleaning the instrument holder.

At step 502, instrument holder 200 can be removed from sterile storage, such as a surgical cabinet or disposable packaging. Individual modules, such as module 202, 204 and 400 can be individually stored and selected for assembling with shaft 206. Individual components of each module can be stored in a disassembled state for assembly immediately before or during a surgical procedure. Alternatively, individual components of each module can be stored in an assembled stated and pre-assembled pre-operatively.

Figure 24A:
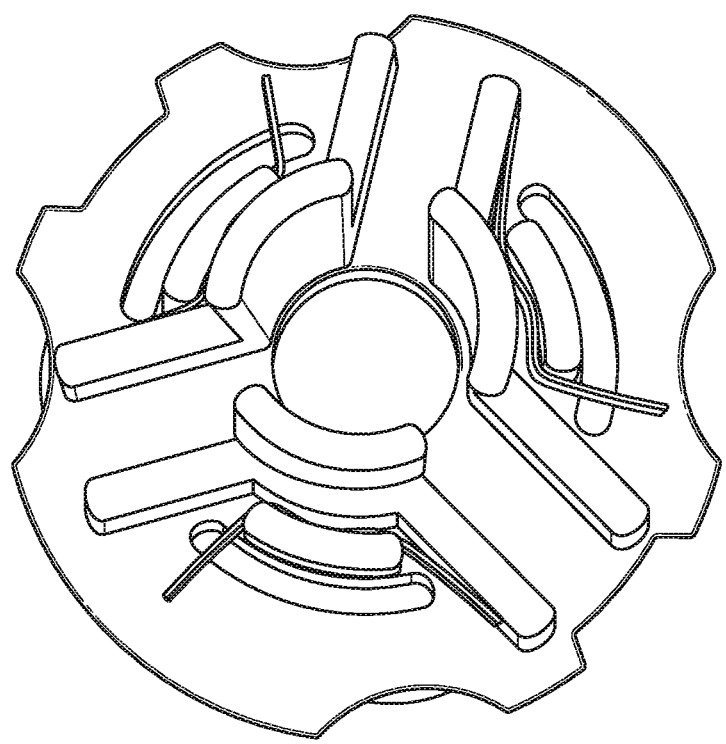
FIGS. 24A-24I shows an example of the first module of FIGS. 5-9 in various states of assembly.

In order to assemble instrument holder 200 for use with first module 202, biasing elements 262 can be assembled with first base 220, as shown in FIG. 24A. For example, curved second sections 316A-316C can be tucked behind pedestals 275A-275C. Positioned as such, straight third sections 318A-318C will be spaced from walls 277 to form spaces 320A-320C.

Figure 24B:
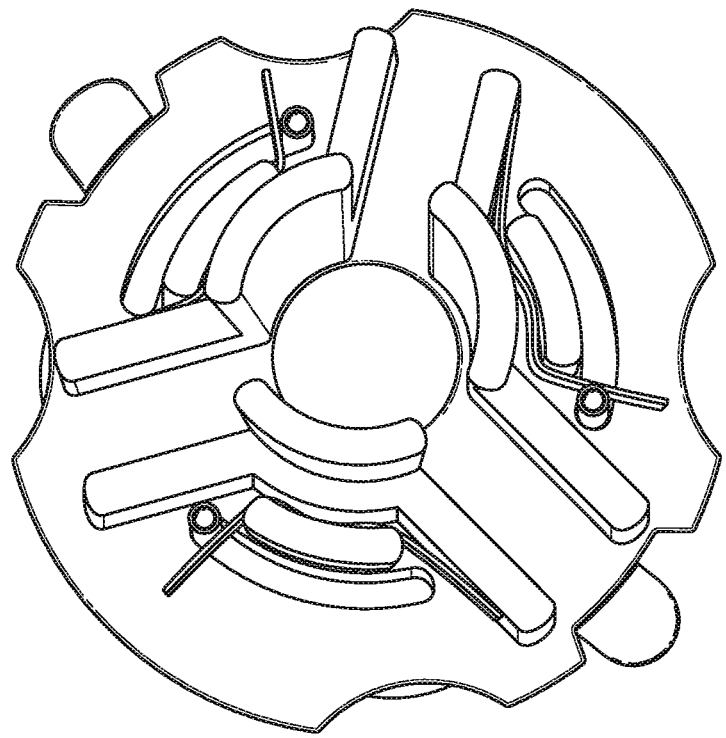

At step 504, tensioner tool 268 can be assembled with first base 220, as shown in FIG. 24B. Specifically, posts 282A-282C can be inserted into channels 273A-273C of first base 220. Posts 282A-282C can be positioned in spaces 320A-320C. Pads 284A-284C on platform 280 can be engaged with the bottom of disk 270 and guides 286A and 286B can be engaged with the side of disk 270.

Figure 24C:
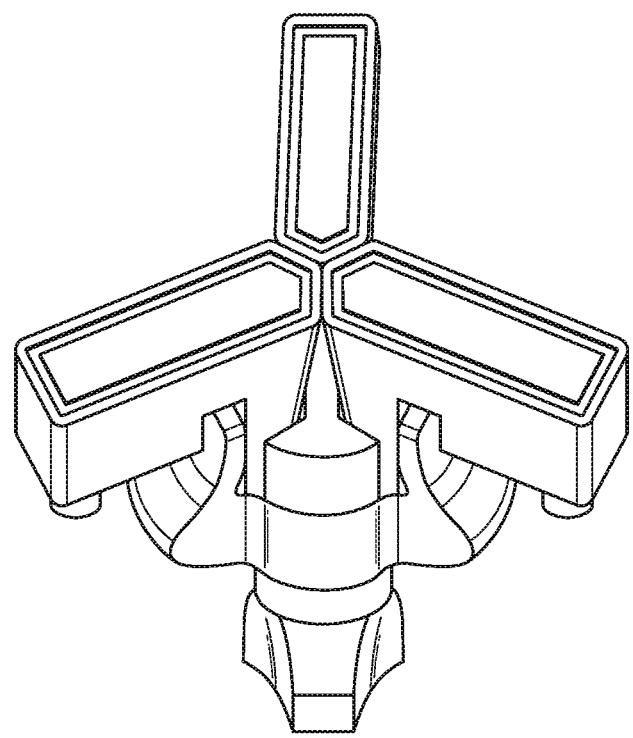

At step 506, teeth 224A-224C can be inserted into tooth holder 266, as shown in FIG. 24C. A user can grip knob 290 in one hand and insert spokes 310A-310C of teeth 224A-224C into sockets 294A-294C of socket portion 292 with the other hand.

Figure 24D:
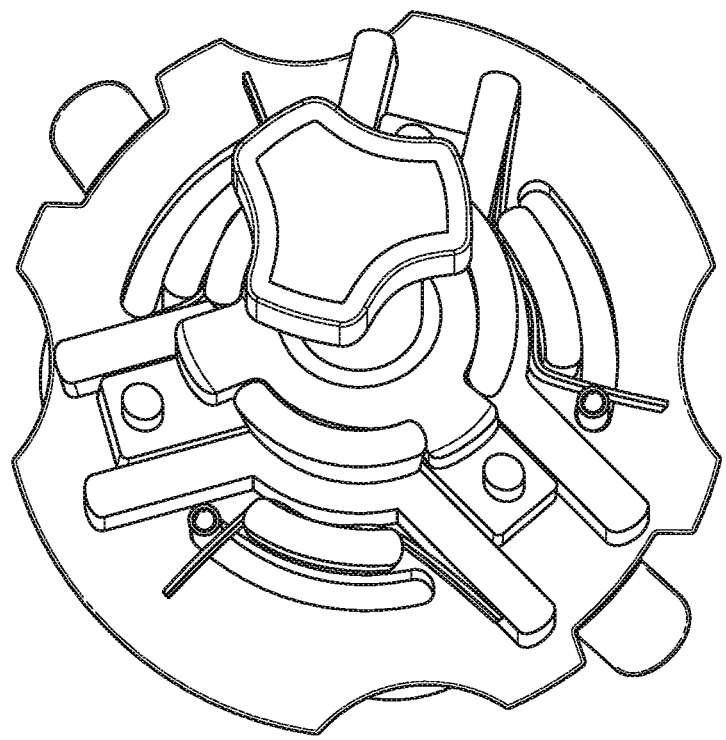

At step 508, teeth 224A-224C can be inserted into slots 260A-260C of base 220 together with tensioner tool 268, as shown in FIG. 24D. A user can align rails 308A-308C with disk portions 276A-276C and spokes 310A-310C with post portions 278A-278C.

Figure 24E:
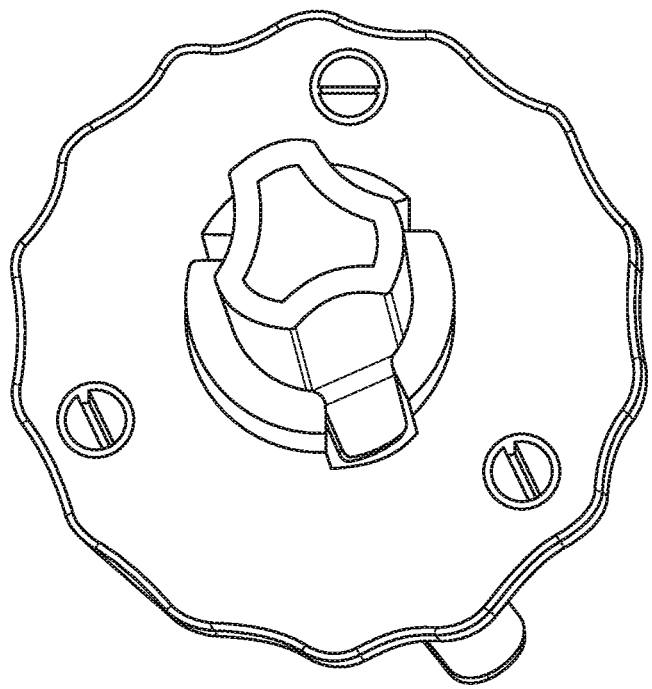

At step 510, cap 222 can be mounted and aligned with teeth 224A-224C while tooth holder 266 is being held, as shown in FIG. 24E.

Figure 24F:
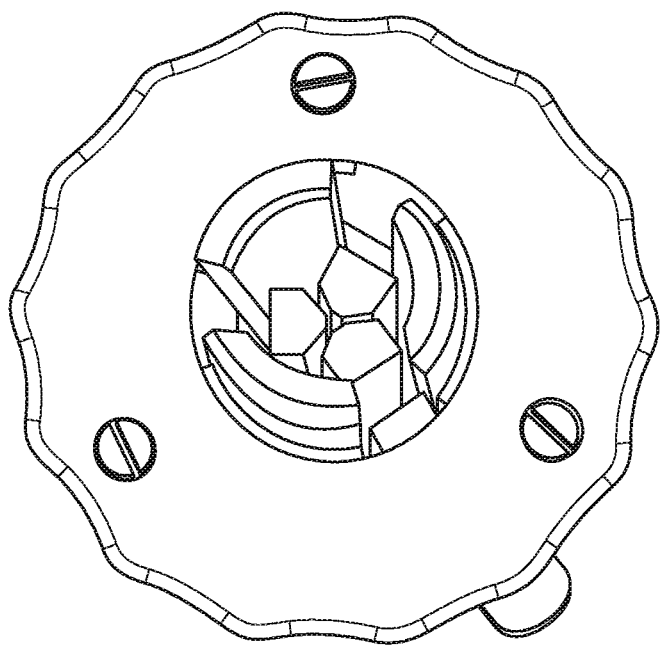

At step 512, tooth holder 266 can be removed from teeth 224A-224C, as shown in FIG. 24F.

Figure 24G:
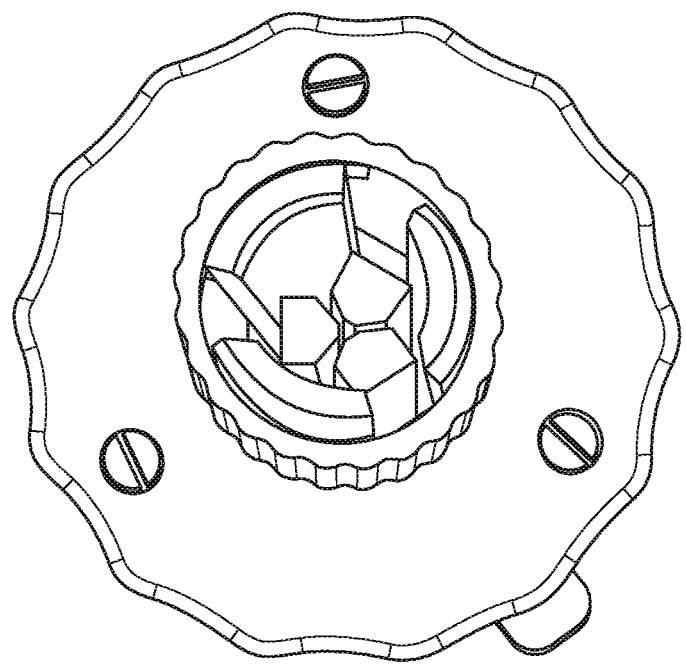

At step 514, fastener 226 can be attached to first base 220, as shown in FIG. 24G.

Figure 24H:
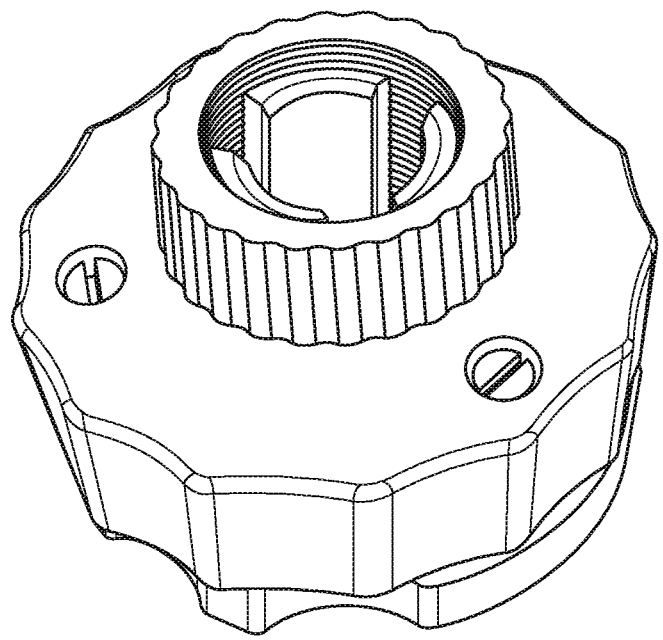

At step 516, tensioner tool 268 can be removed from base 220, as shown in FIG. 24H. Removal of tensioner tool 268 can allow biasing members 262A-262C to retract teeth 224A-224C to a closed position, thereby closing passage 208.

Figure 24I:
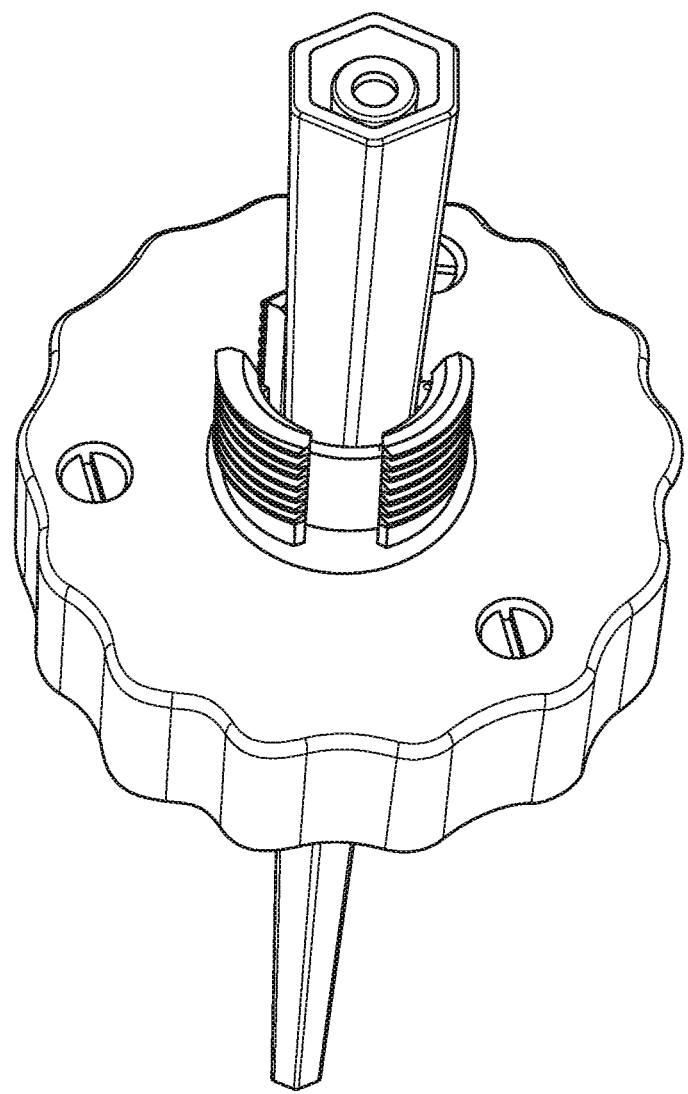

At step 518, first base 220 and tensioner tool 268 can be rotated relative to each other to widen spaces 320A-320C to facilitate assembly with an instrument, as shown in FIG. 24I (fastener 226 not shown in FIG. 24I for clarity). Disk 270 of base 220 can be gripped with the other hand of the user and disk 270 can be rotated to engage guides 286A and 286B with cut-outs 322A and 322B, respectively, to open spaces 320A-320C.

As such, first module is ready to be used in a procedure to hold or guide an instrument, such as instrument 218. Assembly of a second of first instrument holder 202 or second instrument holder 204 to shaft 206 can also be completed, such as by repeating some or all of steps 502-516. Thus, steps 502-516 can describe a method of assembling an instrument holder including a sub-method of assembling an individual module of an instrument holder.

Steps 518-520 can describe a method of performing a medical procedure involving sequentially attaching one or more instruments of different sizes to an adjustable instrument holder.

At step 520, instrument 218 can be inserted into instrument holder 202. Instrument 218 can be positioned in passage 208 and cap 222 can be released to bring teeth 224A-224C in close proximity to, into contact with, or into force against instrument 218, such as under operation of biasing elements 262A-262C. As such, instrument 218 can be guided, held in place or immobilized. Furthermore, fastener 226 can be used as a safety measure to secure 224A-224C in place.

At step 522, fastener 226 can be tightened against cap 222 via threaded engagement with post 274. Fastener 226 can immobilize cap 222 to hold teeth 224A-224C in the desired position set at step 520.

At step 524, a medical procedure or a step of a medical procedure can be performed with instrument 218 held in a desired orientation, such as an orientation according to a medical plan. After the medical procedure or step has been completed, instrument 218 can be removed from first module 202. First, fastener 226 can be disengaged from cap 222 by loosening the threaded engagement with post 274. Release of cap 222 by fastener 226 can result in biasing members 262A-262C moving teeth 224A-224C to a closed position toward axis 210 and instrument 218. As such, another instrument can be assembled to or guided with first module 202. The robotic arm, e.g. robotic arm 120 of FIG. 2, can be repositioned and then a subsequent instrument can be attached to first module 202 by repeating steps 518-524.

At step 526, instrument holder 200 can be disassembled. Fastener 226 can be removed from post 274. Subsequently, cap 222 can be removed from post 274. Teeth 224A-224C can be removed from slots 260A-260C, with or without the use of tooth holder 266. Biasing elements 262A-262C can be removed from engagement with pedestals 275A-275C.

At step 528, the disassembled components of instrument holder 202, e.g., base 202, cap 222, teeth 224A-224C, biasing elements 262A-262C and fastener 226 can be cleaned, sterilized, packaged and stored for later use in a different medical procedure. The disassembled components can be reassembled by repeating steps 502-516.

Figure 22:
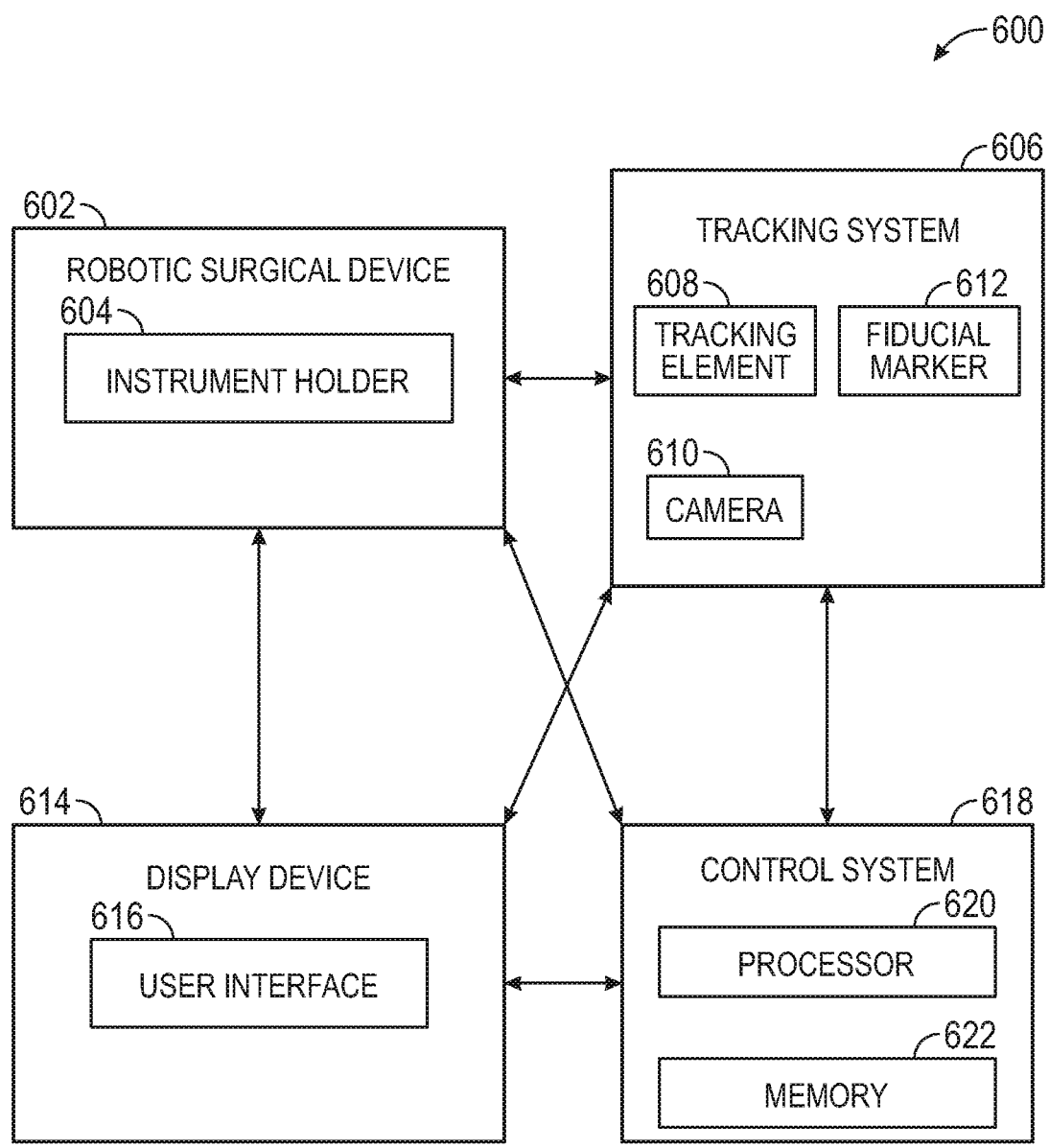
FIG. 22 is a schematic illustration of a robotic surgical system incorporating an instrument holder of the present application interacting with a tracking system.

FIG. 22 illustrates system 600 for performing techniques described herein, in accordance with some embodiments. System 600 can include robotic surgical device 602 coupled to adjustable instrument holder 604 (e.g., instrument holder 202), which may interact with tracking system 606. Tracking system 606 can include tracking element 608, camera 610 and fiducial marker 612. System 600 can include display device 614, which can be used to display user interface 616. System 600 can include control system 618 (e.g., a robotic controller), including processor 620 and memory 622. In an example, display device 614 can be coupled to one or more of robotic surgical device 602, probe device 606, or control system 618.

Figure 23:
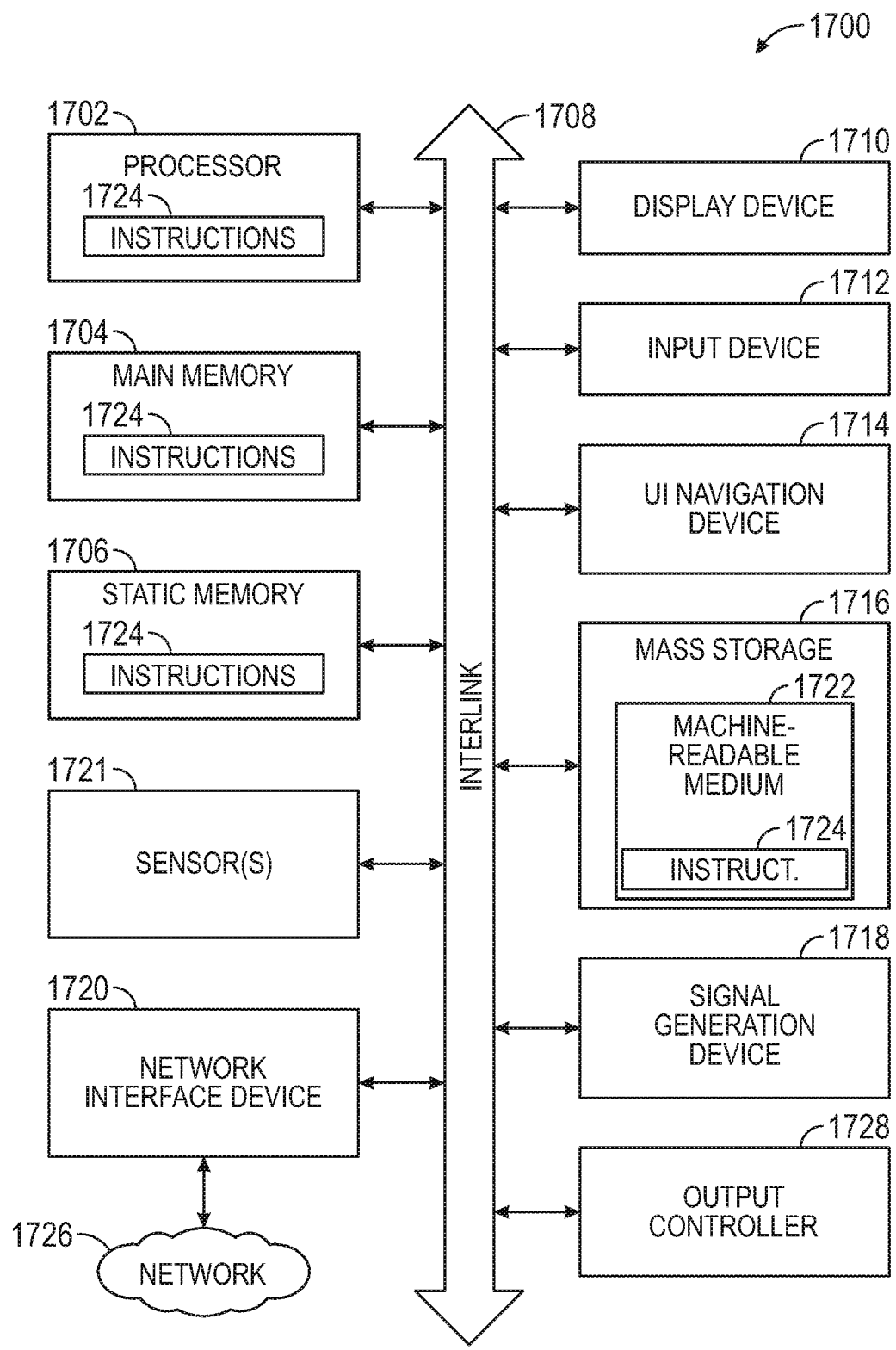
FIG. 23 is a schematic illustration of a block diagram of an example machine upon which any one or more of the techniques discussed herein may perform and with which any of the devices discussed herein may be used in accordance with some embodiments.

FIG. 23 illustrates a block diagram of an example machine 1700 upon which any one or more of the techniques discussed herein may perform in accordance with some embodiments. In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing robotic-assisted surgical procedures that utilize robotic surgical arms that can be coupled to instrument holders used to precisely align trajectories of instruments relative to anatomy of a patient registered to the space of an operating room. The present disclosure describes adjustable instrument holders that can remain mounted to a robotic surgical arm throughout a surgical procedure. The adjustable instrument holders can be adjusted to hold instruments of different sizes, e.g., different diameters, without removing the instrument holder form the robotic arm. The adjustable instrument holders can be easily and quickly manipulated to remove a first instrument of a first size and insert a second instrument of a second size, thereby decreasing time for performing a surgical procedure. The adjustable instrument holders can include passages that have variable orifice sizes, e.g., variable diameters, formed by adjustable members, such as jaws or blades, that form adjustable jaws, chucks or diaphragms to align an instrument and hold an instrument along a trajectory. The adjustable instrument holders can include adjustment members that provide axial length along an axis of the trajectory to provide stability to the instrument. The adjustable instrument holders can additionally be easily and quickly assembled and disassembled for cleaning, sanitizing and sterilizing procedures.

Various Notes & Examples

Example 1 can include or use subject matter such as an instrument holder system that can comprise a base comprising a disk including a central bore, an annular post extending from the disk along an axis to form an annulus surrounding the central bore, and a plurality of guide slots, each of the plurality of guide slots can comprise a disk portion extending in a radial direction along the disk and a post portion extending an axial direction along the annular post; a plurality of teeth positioned in the plurality of guide slots, respectively, each tooth can comprise a rail for movement in the disk portion, a spoke extending from the rail for movement in the post portion and a tab extending from the rail; and a cap comprising a cover portion configured to cover the base, the cover including an aperture to receive the annular post and a plurality of positioning slots disposed in the cover configured to receive the tabs of the plurality of teeth, respectively, wherein each positioning slot can be disposed oblique to the radial direction such that rotation of the cap causes the rail of each tooth to move in a respective one of the disk portions of the plurality of guide slots so that the spoke of each tooth moves relative to the annulus.

Example 2 can include, or can optionally be combined with the subject matter of Example 1, to optionally include each positioning slot of the plurality of positioning slots comprising a circular arc segment having a radius of curvature center eccentric with the axis.

Example 3 can include, or can optionally be combined with the subject matter of one or any combination of Examples 1 or 2 to optionally include each positioning slot of the plurality of positioning slots comprising a straight segment extending at a forty-five-degree angle relative to the radial direction.

Example 4 can include, or can optionally be combined with the subject matter of one or any combination of Examples 1 through 3 to optionally include a fastener that can be engaged with the annular post to retain the cap with the base.

Example 5 can include, or can optionally be combined with the subject matter of one or any combination of Examples 1 through 4 to optionally include a biasing mechanism that can bias the cap into a position where the plurality of teeth is withdrawn from the annulus Example 6 can include, or can optionally be combined with the subject matter of one or any combination of Examples 1 through 5 to optionally include a biasing mechanism that can comprise a plurality of pegs extending from the cap and a plurality of spring elements connected to the base to push against the plurality of pegs, respectively.

Example 7 can include, or can optionally be combined with the subject matter of one or any combination of Examples 1 through 6 to optionally include a tensioner tool that can be configured to adjust the plurality of spring elements to facilitate insertion of the plurality of teeth into the plurality of slots.

Example 8 can include, or can optionally be combined with the subject matter of one or any combination of Examples 1 through 7 to optionally include a tensioner tool that can comprise a platform and a plurality of posts extending from the platform, and a base that can further comprise a plurality of channels extending through the disk to receive the plurality of posts to allow the plurality of posts to engage the plurality of spring elements.

Example 9 can include, or can optionally be combined with the subject matter of one or any combination of Examples 1 through 8 to optionally include a tensioner tool that can further comprise a pair of guides extending from a periphery of the platform to engage the disk of the base of the instrument holder and a plurality of slide pads extending from the platform.

Example 10 can include, or can optionally be combined with the subject matter of one or any combination of Examples 1 through 9 to optionally include a base that can further comprise a plurality of arcuate pedestals to retain the plurality of spring elements.

Example 11 can include, or can optionally be combined with the subject matter of one or any combination of Examples 1 through 10 to optionally include a cartridge configured to hold the plurality of teeth for loading into the plurality of slots.

Example 12 can include, or can optionally be combined with the subject matter of one or any combination of Examples 1 through 11 to optionally include a cartridge that can comprise a handle shaft and a socket portion connected to the handle shaft, the socket portion comprising one socket for each of the spokes of the plurality of teeth.

Example 13 can include or use subject matter such as an instrument holder assembly for use with a robotic surgical system that can comprise a main shaft for assembling to an arm of the robotic surgical system that can comprise a first end, a second end and a central passage extending between the first end and the second end; a first instrument module couplable to the first end of the main shaft that can comprise a first variable diameter jaw configured to hold or guide a portion of an instrument extending from the central passage at the first end, and a second instrument module couplable to the second end of the main shaft that can comprise a second variable diameter jaw configured to hold or guide a portion of the instrument extending from the central passage at the second end.

Example 14 can include, or can optionally be combined with the subject matter of Example 13, to optionally include each of the first and second instrument modules comprising a base couplable to the main shaft at an opening that aligns with the central passage, teeth forming the variable diameter first and second jaws, the teeth mounted on the base to slide along the base to enter the central passage and a cap coupled to the base to engage the teeth, the cap configured to be rotated to cause movement of the teeth.

Example 15 can include, or can optionally be combined with the subject matter of one or any combination of Examples 13 or 14 to optionally include each of the first and second instrument modules that can further comprise a fastener to secure the cap in place to fix the teeth into position.

Example 16 can include, or can optionally be combined with the subject matter of one or any combination of Examples 13 through 15 to optionally include each of the first and second instrument modules further comprising a biasing mechanism to bias the teeth into an open position away from a center axis of the central passage.

Example 17 can include, or can optionally be combined with the subject matter of one or any combination of Examples 13 through 16 to optionally include a main shaft that can further comprise a threaded socket located at the first end, a threaded nut coupled to the first threaded socket, a threaded extension extending from the second end and a fastener extending into the main shaft to extend into the central passage.

Example 18 can include or use subject matter such as a method of assembling an adjustable, pre-tensioned instrument holder that can comprise inserting posts of a tensioner tool into channels of a disk of an instrument holder, positioning the posts against biasing members of the instrument holder, rotating the tensioner tool relative to the instrument holder to move the biasing members with the posts, inserting teeth into slots of the instrument holder and releasing tension in the biasing members such that the biasing members push the teeth into or away from a passage of the instrument holder.

Example 19 can include, or can optionally be combined with the subject matter of Example 18, to optionally include inserting teeth into slots of the instrument holder via inserting a plurality of the teeth into a cartridge and inserting the plurality of teeth into the slots using the cartridge Example 20 can include, or can optionally be combined with the subject matter of one or any combination of Examples 18 or 19 to optionally include removing the cartridge from the plurality of teeth and assembling a cap to the disk to retain the plurality of teeth in the slots.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An instrument holder system comprising:
   a base comprising:
      a disk including a central bore;
      an annular post extending from the disk along an axis to form an annulus surrounding the central bore; and
      a plurality of guide slots, each of the plurality of guide slots comprising:
         a disk portion extending in a radial direction along the disk; and
         a post portion extending an axial direction along the annular post;
   a plurality of teeth positioned in the plurality of guide slots, respectively, each tooth comprising:
      a rail for movement in the disk portion;
      a spoke extending from the rail for movement in the post portion; and
      a tab extending from the rail; and
   a cap comprising:
      a cover portion configured to cover the base, the cover including an aperture to receive the annular post; and
      a plurality of positioning slots disposed in the cover configured to receive the tabs of the plurality of teeth, respectively;
   wherein each positioning slot is disposed oblique to the radial direction such that rotation of the cap causes the rail of each tooth to move in a respective one of the disk portions of the plurality of guide slots so that the spoke of each tooth moves relative to the annulus.

2. The instrument holder system of claim 1, wherein each positioning slot of the plurality of positioning slots comprises a circular arc segment having a radius of curvature center eccentric with the axis.

3. The instrument holder system of claim 1, wherein each positioning slot of the plurality of positioning slots comprises a straight segment extending at a forty-five-degree angle relative to the radial direction.

4. The instrument holder system of claim 1, further comprising a fastener engaged with the annular post to retain the cap with the base.

5. The instrument holder system of claim 1, further comprising a biasing mechanism to bias the cap into a position where the plurality of teeth is withdrawn from the annulus.

6. The instrument holder system of claim 5, wherein the biasing mechanism comprises:
   a plurality of pegs extending from the cap; and
   a plurality of spring elements connected to the base to push against the plurality of pegs, respectively.

7. The instrument holder system of claim 6, further comprising a tensioner tool configured to adjust the plurality of spring elements to facilitate insertion of the plurality of teeth into the plurality of slots.

8. The instrument holder system of claim 7, wherein:
the tensioner tool comprises:
   a platform; and
   a plurality of posts extending from the platform; and
the base further comprises a plurality of channels extending through the disk to receive the plurality of posts to allow the plurality of posts to engage the plurality of spring elements.

9. The instrument holder system of claim 8, wherein the tensioner tool further comprises:
   a pair of guides extending from a periphery of the platform to engage the disk of the base of the instrument holder; and
   a plurality of slide pads extending from the platform.

10. The instrument of claim 6, wherein the base further comprises a plurality of arcuate pedestals to retain the plurality of spring elements.

11. The instrument holder system of claim 1, further comprising a cartridge configured to hold the plurality of teeth for loading into the plurality of slots.

12. The instrument holder system of claim 11, wherein the cartridge comprises:
   a handle shaft; and
   a socket portion connected to the handle shaft, the socket portion comprising one socket for each of the spokes of the plurality of teeth.

13. An instrument holder assembly for use with a robotic surgical system, the instrument holder assembly comprising:
   a main shaft for assembling to an arm of the robotic surgical system, the main shaft comprising:
      a first end;
      a second end; and
      a central passage extending between the first end and the second end;
   a first instrument module couplable to the first end of the main shaft, the first instrument module comprising a first variable diameter jaw configured to hold or guide a portion of an instrument extending from the central passage at the first end; and
   a second instrument module couplable to the second end of the main shaft, the second instrument module comprising a second variable diameter jaw configured to hold or guide a portion of the instrument extending from the central passage at the second end.

14. The instrument holder assembly of claim 13, wherein each of the first and second instrument modules comprises:
   a base couplable to the main shaft at an opening that aligns with the central passage;
   teeth forming the variable diameter first and second jaws, the teeth mounted on the base to slide along the base to enter the central passage; and
   a cap coupled to the base to engage the teeth, the cap configured to be rotated to cause movement of the teeth.

15. The instrument holder assembly of claim 14, wherein each of the first and second instrument modules further comprises a fastener to secure the cap in place to fix the teeth into position.

16. The instrument holder assembly of claim 14, wherein each of the first and second instrument modules further comprises a biasing mechanism to bias the teeth into an open position away from a center axis of the central passage.

17. The instrument holder assembly of claim 13, wherein the main shaft further comprises:
   a threaded socket located at the first end;
   a threaded nut coupled to the first threaded socket;
   a threaded extension extending from the second end; and
   a fastener extending into the main shaft to extend into the central passage.

18. A method of assembling an adjustable, pre-tensioned instrument holder, the method comprising:
   inserting posts of a tensioner tool into channels of a disk of an instrument holder;
   positioning the posts against biasing members of the instrument holder;
   rotating the tensioner tool relative to the instrument holder to move the biasing members with the posts;
   inserting teeth into slots of the instrument holder; and
   releasing tension in the biasing members such that the biasing members push the teeth into or away from a passage of the instrument holder.

19. The method of claim 18, wherein inserting teeth into slots of the instrument holder comprises:
   inserting a plurality of the teeth into a cartridge; and
   inserting the plurality of teeth into the slots using the cartridge.

20. The method of claim 19, further comprising:
   removing the cartridge from the plurality of teeth; and
   assembling a cap to the disk to retain the plurality of teeth in the slots.

* * * * *